(12) United States Patent
Bakos

(10) Patent No.: US 8,480,657 B2
(45) Date of Patent: Jul. 9, 2013

(54) DETACHABLE DISTAL OVERTUBE SECTION AND METHODS FOR FORMING A SEALABLE OPENING IN THE WALL OF AN ORGAN

(75) Inventor: Gregory J. Bakos, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1342 days.

(21) Appl. No.: 11/981,070

(22) Filed: Oct. 31, 2007

(65) Prior Publication Data

US 2009/0112062 A1    Apr. 30, 2009

(51) Int. Cl.
*A61B 17/00* (2006.01)
*A61B 1/04* (2006.01)
*A61F 2/02* (2006.01)
*A61M 5/32* (2006.01)

(52) U.S. Cl.
USPC ............... 606/1; 600/114; 600/30; 606/207; 604/175

(58) Field of Classification Search
USPC ............ 606/1, 10, 214, 115, 213, 215–221, 606/207; 600/158, 106, 37, 114, 16, 115, 600/104, 435, 7, 204, 30; 604/66, 502, 256, 604/528, 176, 616, 191, 506, 510, 175
See application file for complete search history.

(56) References Cited

U.S. PATENT DOCUMENTS

| | | | |
|---|---|---|---|
| 645,576 A | 3/1900 | Telsa | |
| 649,621 A | 5/1900 | Tesla | |
| 787,412 A | 4/1905 | Tesla | |
| 1,127,948 A | 2/1915 | Wappler | |
| 1,482,653 A | 2/1924 | Lilly | |
| 1,625,602 A | 4/1927 | Gould et al. | |
| 1,916,722 A | 7/1933 | Ende | |
| 2,028,635 A | 1/1936 | Wappler | |
| 2,031,682 A | 2/1936 | Wappler et al. | |
| 2,113,246 A | 4/1938 | Wappler | |
| 2,155,365 A | 4/1939 | Rankin | |
| 2,191,858 A | 2/1940 | Moore | |
| 2,196,620 A | 4/1940 | Attarian | |
| 2,388,137 A | 10/1945 | Graumlich | |
| 2,493,108 A | 1/1950 | Casey, Jr. | |

(Continued)

FOREIGN PATENT DOCUMENTS

AU    666310 B2    2/1996
DE    3008120 A1    9/1980

(Continued)

OTHER PUBLICATIONS

K. Sumiyama et al., "Endoscopic Caps," Tech. Gastrointest. Endosc., vol. 8, pp. 28-32, 2006.

(Continued)

*Primary Examiner* — John P Leubecker
*Assistant Examiner* — Ronald D Colque

(57) ABSTRACT

An overtube for use with an endoscopic surgical instrument. In various embodiments, the overtube may comprise a hollow tubular member that has an implantable tip detachably affixed to a distal end thereof. The implantable tip may have at least one retention member formed thereon to retain the tip within an organ wall. The implantable tip may further have a lumen extending therethrough to form a passageway through the organ wall. A plug member may be provided to selectively seal off the lumen within the implantable tip.

5 Claims, 6 Drawing Sheets

U.S. PATENT DOCUMENTS

| | | | |
|---|---|---|---|
| 2,504,152 A | 4/1950 | Riker et al. | |
| 2,938,382 A | 5/1960 | De Graaf | |
| 2,952,206 A | 9/1960 | Becksted | |
| 3,069,195 A | 12/1962 | Buck | |
| 3,070,088 A | 12/1962 | Brahos | |
| 3,170,471 A | 2/1965 | Schnitzer | |
| 3,435,824 A | 4/1969 | Gamponia | |
| 3,470,876 A | 10/1969 | Barchilon | |
| 3,595,239 A | 7/1971 | Petersen | |
| 3,669,487 A | 6/1972 | Roberts et al. | |
| 3,746,881 A | 7/1973 | Fitch et al. | |
| 3,799,672 A | 3/1974 | Vurek | |
| 3,854,473 A | 12/1974 | Matsuo | |
| 3,946,740 A | 3/1976 | Bassett | |
| 3,948,251 A | 4/1976 | Hosono | |
| 3,994,301 A | 11/1976 | Agris | |
| 4,011,872 A | 3/1977 | Komiya | |
| 4,012,812 A | 3/1977 | Black | |
| 4,085,743 A | 4/1978 | Yoon | |
| 4,164,225 A | 8/1979 | Johnson et al. | |
| 4,174,715 A | 11/1979 | Hasson | |
| 4,178,920 A | 12/1979 | Cawood, Jr. et al. | |
| 4,207,873 A | 6/1980 | Kruy | |
| 4,235,238 A | 11/1980 | Ogiu et al. | |
| 4,258,716 A | 3/1981 | Sutherland | |
| 4,269,174 A | 5/1981 | Adair | |
| 4,278,077 A | 7/1981 | Mizumoto | |
| 4,285,344 A | 8/1981 | Marshall | |
| 4,311,143 A | 1/1982 | Komiya | |
| 4,329,980 A | 5/1982 | Terada | |
| 4,396,021 A | 8/1983 | Baumgartner | |
| 4,406,656 A | 9/1983 | Hattler et al. | |
| 4,452,246 A | 6/1984 | Bader et al. | |
| 4,461,281 A | 7/1984 | Carson | |
| 4,491,132 A | 1/1985 | Aikins | |
| 4,527,331 A | 7/1985 | Lasner et al. | |
| 4,527,564 A | 7/1985 | Eguchi et al. | |
| 4,538,594 A | 9/1985 | Boebel et al. | |
| D281,104 S | 10/1985 | Davison | |
| 4,569,347 A | 2/1986 | Frisbie | |
| 4,580,551 A | 4/1986 | Siegmund et al. | |
| 4,646,722 A | 3/1987 | Silverstein et al. | |
| 4,653,476 A | 3/1987 | Bonnet | |
| 4,655,219 A | 4/1987 | Petruzzi | |
| 4,669,470 A | 6/1987 | Brandfield | |
| 4,671,477 A | 6/1987 | Cullen | |
| 4,685,447 A | 8/1987 | Iversen et al. | |
| 4,711,240 A | 12/1987 | Goldwasser et al. | |
| 4,712,545 A | 12/1987 | Honkanen | |
| 4,721,116 A | 1/1988 | Schintgen et al. | |
| 4,733,662 A | 3/1988 | DeSatnick et al. | |
| D295,894 S | 5/1988 | Sharkany et al. | |
| 4,763,669 A | 8/1988 | Jaeger | |
| 4,770,188 A | 9/1988 | Chikama | |
| 4,815,450 A | 3/1989 | Patel | |
| 4,823,794 A | 4/1989 | Pierce | |
| 4,829,999 A | 5/1989 | Auth | |
| 4,867,140 A | 9/1989 | Hovis et al. | |
| 4,869,238 A | 9/1989 | Opie et al. | |
| 4,869,459 A | 9/1989 | Bourne | |
| 4,873,979 A | 10/1989 | Hanna | |
| 4,880,015 A | 11/1989 | Nierman | |
| 4,911,148 A | 3/1990 | Sosnowski et al. | |
| 4,926,860 A | 5/1990 | Stice et al. | |
| 4,938,214 A | 7/1990 | Specht et al. | |
| 4,950,273 A | 8/1990 | Briggs | |
| 4,950,285 A | 8/1990 | Wilk | |
| 4,960,133 A | 10/1990 | Hewson | |
| 4,977,887 A | 12/1990 | Gouda | |
| 4,979,950 A | 12/1990 | Transue et al. | |
| 4,984,581 A | 1/1991 | Stice | |
| 4,994,079 A | 2/1991 | Genese et al. | |
| 5,007,917 A | 4/1991 | Evans | |
| 5,010,876 A | 4/1991 | Henley et al. | |
| 5,020,514 A | 6/1991 | Heckele | |
| 5,020,535 A | 6/1991 | Parker et al. | |
| 5,025,778 A | 6/1991 | Silverstein et al. | |
| 5,033,169 A | 7/1991 | Bindon | |
| 5,037,433 A | 8/1991 | Wilk et al. | |
| 5,041,129 A | 8/1991 | Hayhurst et al. | |
| 5,046,513 A | 9/1991 | Gatturna et al. | |
| 5,050,585 A | 9/1991 | Takahashi | |
| 5,052,372 A | 10/1991 | Shapiro | |
| 5,065,516 A | 11/1991 | Dulebohn | |
| 5,066,295 A | 11/1991 | Kozak et al. | |
| 5,108,421 A * | 4/1992 | Fowler | 606/213 |
| 5,123,913 A | 6/1992 | Wilk et al. | |
| 5,123,914 A | 6/1992 | Cope | |
| 5,133,727 A | 7/1992 | Bales et al. | |
| 5,147,374 A | 9/1992 | Fernandez | |
| 5,174,300 A | 12/1992 | Bales et al. | |
| 5,176,126 A | 1/1993 | Chikama | |
| 5,190,050 A | 3/1993 | Nitzsche | |
| 5,190,555 A | 3/1993 | Wetter et al. | |
| 5,192,284 A | 3/1993 | Pleatman | |
| 5,192,300 A * | 3/1993 | Fowler | 606/213 |
| 5,201,752 A | 4/1993 | Brown et al. | |
| 5,201,908 A | 4/1993 | Jones | |
| 5,203,785 A | 4/1993 | Slater | |
| 5,203,787 A | 4/1993 | Noblitt et al. | |
| 5,209,747 A | 5/1993 | Knoepfler | |
| 5,217,003 A | 6/1993 | Wilk | |
| 5,217,453 A | 6/1993 | Wilk | |
| 5,219,357 A | 6/1993 | Honkanen et al. | |
| 5,219,358 A | 6/1993 | Bendel et al. | |
| 5,222,362 A | 6/1993 | Maus et al. | |
| 5,222,965 A | 6/1993 | Haughton | |
| 5,234,437 A | 8/1993 | Sepetka | |
| 5,234,453 A | 8/1993 | Smith et al. | |
| 5,235,964 A | 8/1993 | Abenaim | |
| 5,242,456 A | 9/1993 | Nash et al. | |
| 5,246,424 A | 9/1993 | Wilk | |
| 5,259,366 A | 11/1993 | Reydel et al. | |
| 5,263,958 A | 11/1993 | deGuillebon et al. | |
| 5,273,524 A | 12/1993 | Fox et al. | |
| 5,275,607 A | 1/1994 | Lo et al. | |
| 5,275,616 A * | 1/1994 | Fowler | 606/213 |
| 5,284,128 A | 2/1994 | Hart | |
| 5,284,162 A | 2/1994 | Wilk | |
| 5,287,845 A | 2/1994 | Faul et al. | |
| 5,287,852 A * | 2/1994 | Arkinstall | 128/207.14 |
| 5,290,299 A | 3/1994 | Fain et al. | |
| 5,290,302 A | 3/1994 | Pericic | |
| 5,295,977 A | 3/1994 | Cohen et al. | |
| 5,297,536 A | 3/1994 | Wilk | |
| 5,301,061 A | 4/1994 | Nakada et al. | |
| 5,312,333 A | 5/1994 | Churinetz et al. | |
| 5,312,351 A | 5/1994 | Gerrone | |
| 5,312,416 A | 5/1994 | Spaeth et al. | |
| 5,312,423 A | 5/1994 | Rosenbluth et al. | |
| 5,318,589 A | 6/1994 | Lichtman | |
| 5,320,636 A | 6/1994 | Slater | |
| 5,324,261 A | 6/1994 | Amundson et al. | |
| 5,325,845 A | 7/1994 | Adair | |
| 5,330,471 A | 7/1994 | Eggers | |
| 5,330,486 A | 7/1994 | Wilk | |
| 5,330,488 A | 7/1994 | Goldrath | |
| 5,330,496 A | 7/1994 | Alferness | |
| 5,330,502 A | 7/1994 | Hassler et al. | |
| 5,331,971 A | 7/1994 | Bales et al. | |
| 5,334,198 A | 8/1994 | Hart et al. | |
| 5,344,428 A | 9/1994 | Griffiths | |
| 5,350,391 A | 9/1994 | Iacovelli | |
| 5,352,184 A | 10/1994 | Goldberg et al. | |
| 5,352,222 A | 10/1994 | Rydell | |
| 5,354,302 A | 10/1994 | Ko | |
| 5,354,311 A | 10/1994 | Kambin et al. | |
| 5,356,381 A * | 10/1994 | Ensminger et al. | 604/288.03 |
| 5,356,408 A | 10/1994 | Rydell | |
| 5,364,408 A | 11/1994 | Gordon | |
| 5,364,410 A | 11/1994 | Failla et al. | |
| 5,366,466 A | 11/1994 | Christian et al. | |
| 5,366,467 A | 11/1994 | Lynch et al. | |
| 5,368,605 A | 11/1994 | Miller, Jr. | |
| 5,370,647 A | 12/1994 | Graber et al. | |
| 5,370,679 A | 12/1994 | Atlee, III | |
| 5,374,273 A | 12/1994 | Nakao et al. | |

| | | |
|---|---|---|
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,443,463 A | 8/1995 | Stern et al. |
| 5,445,638 A | 8/1995 | Rydell et al. |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,478,352 A * | 12/1995 | Fowler .......................... 606/213 |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,536,248 A | 7/1996 | Weaver et al. |
| 5,538,509 A | 7/1996 | Dunlap et al. |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A * | 11/1996 | Yoon .......................... 606/139 |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,591,205 A * | 1/1997 | Fowler .......................... 606/213 |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,601,602 A * | 2/1997 | Fowler .......................... 606/213 |
| 5,604,531 A | 2/1997 | Iddan et al. |
| 5,607,389 A | 3/1997 | Edwards et al. |
| 5,607,406 A | 3/1997 | Hernandez et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A * | 7/1997 | Rudd et al. .................... 606/213 |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,716,375 A * | 2/1998 | Fowler .......................... 606/213 |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,746,759 A | 5/1998 | Meade et al. |
| 5,749,826 A * | 5/1998 | Faulkner ........................ 600/29 |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |

| | | | | | | |
|---|---|---|---|---|---|---|
| 5,817,107 A | 10/1998 | Schaller | | 6,053,927 A | 4/2000 | Hamas |
| 5,817,119 A | 10/1998 | Klieman et al. | | 6,066,160 A | 5/2000 | Colvin et al. |
| 5,819,736 A | 10/1998 | Avny et al. | | 6,068,603 A | 5/2000 | Suzuki |
| 5,823,947 A | 10/1998 | Yoon et al. | | 6,068,629 A | 5/2000 | Haissaguerre et al. |
| 5,824,071 A * | 10/1998 | Nelson et al. ............ 606/194 | | 6,071,233 A | 6/2000 | Ishikawa et al. |
| 5,827,281 A | 10/1998 | Levin | | 6,074,408 A | 6/2000 | Freeman |
| 5,827,299 A | 10/1998 | Thomason et al. | | 6,086,530 A | 7/2000 | Mack |
| 5,830,231 A | 11/1998 | Geiges, Jr. | | 6,090,105 A | 7/2000 | Zepeda et al. |
| 5,833,700 A | 11/1998 | Fogelberg et al. | | 6,090,108 A | 7/2000 | McBrayer et al. |
| 5,833,703 A | 11/1998 | Manushakian | | 6,090,129 A | 7/2000 | Ouchi |
| 5,843,017 A | 12/1998 | Yoon | | 6,096,046 A | 8/2000 | Weiss |
| 5,843,121 A | 12/1998 | Yoon | | 6,102,926 A | 8/2000 | Tartaglia et al. |
| 5,849,022 A | 12/1998 | Sakashita et al. | | 6,106,473 A | 8/2000 | Violante et al. |
| 5,853,374 A | 12/1998 | Hart et al. | | 6,109,852 A | 8/2000 | Shahinpoor et al. |
| 5,855,585 A | 1/1999 | Kontos | | 6,110,154 A | 8/2000 | Shimomura et al. |
| 5,860,913 A | 1/1999 | Yamaya et al. | | 6,110,183 A | 8/2000 | Cope |
| 5,860,995 A | 1/1999 | Berkelaar | | 6,113,593 A | 9/2000 | Tu et al. |
| 5,868,762 A | 2/1999 | Cragg et al. | | 6,117,144 A | 9/2000 | Nobles et al. |
| 5,876,411 A | 3/1999 | Kontos | | 6,117,158 A | 9/2000 | Measamer et al. |
| 5,882,331 A | 3/1999 | Sasaki | | 6,139,555 A | 10/2000 | Hart et al. |
| 5,882,344 A | 3/1999 | Stouder, Jr. | | 6,141,037 A | 10/2000 | Upton et al. |
| 5,893,846 A | 4/1999 | Bales et al. | | 6,146,391 A | 11/2000 | Cigaina |
| 5,893,874 A | 4/1999 | Bourque et al. | | 6,148,222 A | 11/2000 | Ramsey, III |
| 5,893,875 A | 4/1999 | O'Connor et al. | | 6,149,653 A | 11/2000 | Deslauriers |
| 5,897,487 A | 4/1999 | Ouchi | | 6,149,662 A | 11/2000 | Pugliesi et al. |
| 5,899,919 A | 5/1999 | Eubanks, Jr. et al. | | 6,156,006 A | 12/2000 | Brosens et al. |
| 5,902,254 A | 5/1999 | Magram | | 6,159,200 A | 12/2000 | Verdura et al. |
| 5,904,702 A | 5/1999 | Ek et al. | | 6,165,184 A | 12/2000 | Verdura et al. |
| 5,908,420 A | 6/1999 | Parins et al. | | 6,168,570 B1 | 1/2001 | Ferrera |
| 5,908,429 A | 6/1999 | Yoon | | 6,168,605 B1 | 1/2001 | Measamer et al. |
| 5,911,737 A | 6/1999 | Lee et al. | | 6,170,130 B1 | 1/2001 | Hamilton et al. |
| 5,916,146 A | 6/1999 | Allotta et al. | | 6,179,776 B1 | 1/2001 | Adams et al. |
| 5,916,147 A | 6/1999 | Boury | | 6,179,837 B1 | 1/2001 | Hooven |
| 5,921,993 A | 7/1999 | Yoon | | 6,183,420 B1 | 2/2001 | Douk et al. |
| 5,921,997 A | 7/1999 | Fogelberg et al. | | 6,190,353 B1 | 2/2001 | Makower et al. |
| 5,922,008 A | 7/1999 | Gimpelson | | 6,190,384 B1 | 2/2001 | Ouchi |
| 5,925,052 A | 7/1999 | Simmons | | 6,190,399 B1 | 2/2001 | Palmer et al. |
| 5,928,255 A | 7/1999 | Meade et al. | | 6,203,533 B1 | 3/2001 | Ouchi |
| 5,928,266 A | 7/1999 | Kontos | | 6,206,872 B1 | 3/2001 | Lafond et al. |
| 5,936,536 A | 8/1999 | Morris | | 6,206,877 B1 | 3/2001 | Kese et al. |
| 5,944,718 A | 8/1999 | Austin et al. | | 6,206,904 B1 | 3/2001 | Ouchi |
| 5,951,547 A | 9/1999 | Gough et al. | | 6,214,007 B1 | 4/2001 | Anderson |
| 5,951,549 A | 9/1999 | Richardson et al. | | 6,228,096 B1 | 5/2001 | Marchand |
| 5,954,720 A | 9/1999 | Wilson et al. | | 6,234,958 B1 | 5/2001 | Snoke et al. |
| 5,954,731 A | 9/1999 | Yoon | | 6,245,079 B1 | 6/2001 | Nobles et al. |
| 5,957,936 A | 9/1999 | Yoon et al. | | 6,246,914 B1 | 6/2001 | de la Rama et al. |
| 5,957,943 A | 9/1999 | Vaitekunas | | 6,258,064 B1 | 7/2001 | Smith et al. |
| 5,957,953 A | 9/1999 | DiPoto et al. | | 6,261,242 B1 | 7/2001 | Roberts et al. |
| 5,964,782 A | 10/1999 | Lafontaine et al. | | 6,264,664 B1 | 7/2001 | Avellanet |
| 5,971,995 A | 10/1999 | Rousseau | | 6,270,497 B1 | 8/2001 | Sekino et al. |
| 5,972,002 A | 10/1999 | Bark et al. | | 6,270,505 B1 | 8/2001 | Yoshida et al. |
| 5,976,074 A | 11/1999 | Moriyama | | 6,277,136 B1 | 8/2001 | Bonutti |
| 5,976,075 A | 11/1999 | Beane et al. | | 6,283,963 B1 | 9/2001 | Regula |
| 5,976,130 A | 11/1999 | McBrayer et al. | | 6,293,909 B1 | 9/2001 | Chu et al. |
| 5,976,131 A | 11/1999 | Guglielmi et al. | | 6,293,952 B1 | 9/2001 | Brosens et al. |
| 5,980,539 A | 11/1999 | Kontos | | 6,296,630 B1 | 10/2001 | Altman et al. |
| 5,980,556 A | 11/1999 | Giordano et al. | | 6,314,963 B1 | 11/2001 | Vaska et al. |
| 5,984,938 A | 11/1999 | Yoon | | 6,322,578 B1 | 11/2001 | Houle et al. |
| 5,984,939 A | 11/1999 | Yoon | | 6,326,177 B1 | 12/2001 | Schoenbach et al. |
| 5,984,950 A | 11/1999 | Cragg et al. | | 6,328,730 B1 | 12/2001 | Harkrider, Jr. |
| 5,989,182 A | 11/1999 | Hori et al. | | 6,350,267 B1 | 2/2002 | Stefanchik |
| 5,993,447 A | 11/1999 | Blewett et al. | | 6,350,278 B1 | 2/2002 | Lenker et al. |
| 5,993,474 A | 11/1999 | Ouchi | | 6,352,503 B1 | 3/2002 | Matsui et al. |
| 5,997,555 A | 12/1999 | Kontos | | 6,352,543 B1 | 3/2002 | Cole |
| 6,001,120 A | 12/1999 | Levin | | 6,355,013 B1 | 3/2002 | van Muiden |
| 6,004,269 A | 12/1999 | Crowley et al. | | 6,355,035 B1 | 3/2002 | Manushakian |
| 6,004,330 A | 12/1999 | Middleman et al. | | 6,361,534 B1 | 3/2002 | Chen et al. |
| 6,007,566 A | 12/1999 | Wenstrom, Jr. | | 6,371,956 B1 | 4/2002 | Wilson et al. |
| 6,010,515 A | 1/2000 | Swain et al. | | 6,379,366 B1 | 4/2002 | Fleischman et al. |
| 6,012,494 A | 1/2000 | Balazs | | 6,383,195 B1 | 5/2002 | Richard |
| 6,017,356 A | 1/2000 | Frederick et al. | | 6,383,197 B1 | 5/2002 | Conlon et al. |
| 6,019,770 A | 2/2000 | Christoudias | | 6,387,671 B1 | 5/2002 | Rubinsky et al. |
| 6,024,708 A | 2/2000 | Bales et al. | | 6,391,029 B1 | 5/2002 | Hooven et al. |
| 6,024,747 A | 2/2000 | Kontos | | 6,398,708 B1 | 6/2002 | Hastings et al. |
| 6,027,522 A | 2/2000 | Palmer | | 6,402,735 B1 | 6/2002 | Langevin |
| 6,030,365 A | 2/2000 | Laufer | | 6,406,440 B1 | 6/2002 | Stefanchik |
| 6,030,634 A | 2/2000 | Wu et al. | | 6,409,727 B1 | 6/2002 | Bales et al. |
| 6,033,399 A | 3/2000 | Gines | | 6,409,733 B1 | 6/2002 | Conlon et al. |
| 6,036,685 A | 3/2000 | Mueller | | 6,419,641 B1 | 7/2002 | Mark et al. |

| | | | | | | |
|---|---|---|---|---|---|---|
| 6,427,089 B1 | 7/2002 | Knowlton | | 6,743,166 B2 | 6/2004 | Berci et al. |
| 6,431,500 B1 | 8/2002 | Jacobs et al. | | 6,743,239 B1 | 6/2004 | Kuehn et al. |
| 6,436,107 B1 | 8/2002 | Wang et al. | | 6,743,240 B2 | 6/2004 | Smith et al. |
| 6,443,970 B1 | 9/2002 | Schulze et al. | | 6,749,560 B1 | 6/2004 | Konstorum et al. |
| 6,443,988 B2 | 9/2002 | Felt et al. | | 6,749,609 B1 | 6/2004 | Lunsford et al. |
| 6,447,511 B1 | 9/2002 | Slater | | 6,752,768 B2 | 6/2004 | Burdorff et al. |
| 6,447,523 B1 | 9/2002 | Middleman et al. | | 6,752,811 B2 | 6/2004 | Chu et al. |
| 6,454,783 B1 | 9/2002 | Piskun | | 6,752,822 B2 | 6/2004 | Jespersen |
| 6,454,785 B2 | 9/2002 | De Hoyos Garza | | 6,758,857 B2 | 7/2004 | Cioanta et al. |
| 6,458,076 B1 | 10/2002 | Pruitt | | 6,761,685 B2 | 7/2004 | Adams et al. |
| 6,464,701 B1 | 10/2002 | Hooven et al. | | 6,761,718 B2 | 7/2004 | Madsen |
| 6,464,702 B2 | 10/2002 | Schulze et al. | | 6,773,434 B2 | 8/2004 | Ciarrocca |
| 6,470,218 B1 | 10/2002 | Behl | | 6,776,787 B2 | 8/2004 | Phung et al. |
| 6,475,104 B1 | 11/2002 | Lutz et al. | | 6,780,151 B2 | 8/2004 | Grabover et al. |
| 6,485,411 B1 | 11/2002 | Konstorum et al. | | 6,780,352 B2 | 8/2004 | Jacobson |
| 6,489,745 B1 | 12/2002 | Koreis | | 6,783,491 B2 | 8/2004 | Saadat et al. |
| 6,491,626 B1 | 12/2002 | Stone et al. | | 6,786,864 B2 | 9/2004 | Matsuura et al. |
| 6,491,627 B1 | 12/2002 | Komi | | 6,790,173 B2 | 9/2004 | Saadat et al. |
| 6,491,691 B1 | 12/2002 | Morley et al. | | 6,790,217 B2 | 9/2004 | Schulze et al. |
| 6,493,590 B1 | 12/2002 | Wessman et al. | | 6,795,728 B2 | 9/2004 | Chornenky et al. |
| 6,494,893 B2 | 12/2002 | Dubrul et al. | | 6,800,056 B2 | 10/2004 | Tartaglia et al. |
| 6,500,176 B1 | 12/2002 | Truckai et al. | | 6,808,491 B2 | 10/2004 | Kortenbach et al. |
| 6,503,192 B1 | 1/2003 | Ouchi | | 6,817,974 B2 | 11/2004 | Cooper et al. |
| 6,506,190 B1 | 1/2003 | Walshe | | 6,824,548 B2 | 11/2004 | Smith et al. |
| 6,508,827 B1 | 1/2003 | Manhes | | 6,836,688 B2 | 12/2004 | Ingle et al. |
| 6,514,239 B2 | 2/2003 | Shimmura et al. | | 6,837,847 B2 | 1/2005 | Ewers et al. |
| 6,520,954 B2 | 2/2003 | Ouchi | | 6,840,938 B1 | 1/2005 | Morley et al. |
| 6,527,782 B2 | 3/2003 | Hogg et al. | | 6,843,794 B2 | 1/2005 | Sixto, Jr. et al. |
| 6,543,456 B1 | 4/2003 | Freeman | | 6,861,250 B1 | 3/2005 | Cole et al. |
| 6,551,270 B1 | 4/2003 | Bimbo et al. | | 6,866,627 B2 | 3/2005 | Nozue |
| 6,554,766 B2 | 4/2003 | Maeda et al. | | 6,866,628 B2 | 3/2005 | Goodman et al. |
| 6,554,829 B2 | 4/2003 | Schulze et al. | | 6,878,106 B1 | 4/2005 | Herrmann |
| 6,558,384 B2 | 5/2003 | Mayenberger | | 6,878,110 B2 | 4/2005 | Yang et al. |
| 6,562,035 B1 | 5/2003 | Levin | | 6,881,216 B2 | 4/2005 | Di Caprio et al. |
| 6,562,052 B2 | 5/2003 | Nobles et al. | | 6,884,213 B2 | 4/2005 | Raz et al. |
| 6,569,159 B1 | 5/2003 | Edwards et al. | | 6,887,255 B2 | 5/2005 | Shimm |
| 6,572,629 B2 | 6/2003 | Kalloo et al. | | 6,889,089 B2 | 5/2005 | Behl et al. |
| 6,572,635 B1 | 6/2003 | Bonutti | | 6,896,683 B1 | 5/2005 | Gadberry et al. |
| 6,575,988 B2 | 6/2003 | Rousseau | | 6,908,427 B2 | 6/2005 | Fleener et al. |
| 6,579,311 B1 | 6/2003 | Makower | | 6,908,476 B2 | 6/2005 | Jud et al. |
| 6,581,889 B2 | 6/2003 | Carpenter et al. | | 6,916,284 B2 | 7/2005 | Moriyama |
| 6,585,642 B2 | 7/2003 | Christopher | | 6,918,871 B2 | 7/2005 | Schulze |
| 6,585,717 B1 | 7/2003 | Wittenberger et al. | | 6,926,725 B2 | 8/2005 | Cooke et al. |
| 6,587,750 B2 | 7/2003 | Gerbi et al. | | 6,932,810 B2 | 8/2005 | Ryan |
| 6,592,559 B1 | 7/2003 | Pakter et al. | | 6,932,824 B1 | 8/2005 | Roop et al. |
| 6,592,603 B2 | 7/2003 | Lasner | | 6,932,827 B2 | 8/2005 | Cole |
| 6,602,262 B2 | 8/2003 | Griego et al. | | 6,936,003 B2 | 8/2005 | Iddan |
| 6,605,105 B1 | 8/2003 | Cuschieri et al. | | 6,939,327 B2 | 9/2005 | Hall et al. |
| 6,610,072 B1 | 8/2003 | Christy et al. | | 6,942,613 B2 | 9/2005 | Ewers et al. |
| 6,610,074 B2 | 8/2003 | Santilli | | 6,944,490 B1 | 9/2005 | Chow |
| 6,620,193 B1 | 9/2003 | Lau et al. | | 6,945,472 B2 | 9/2005 | Wuttke et al. |
| 6,623,448 B2 | 9/2003 | Slater | | 6,945,979 B2 | 9/2005 | Kortenbach et al. |
| 6,626,919 B1 | 9/2003 | Swanstrom | | 6,958,035 B2 | 10/2005 | Friedman et al. |
| 6,632,229 B1 | 10/2003 | Yamanouchi | | 6,960,162 B2 | 11/2005 | Saadat et al. |
| 6,638,286 B1 | 10/2003 | Burbank et al. | | 6,960,163 B2 | 11/2005 | Ewers et al. |
| 6,645,225 B1 * | 11/2003 | Atkinson ............... 606/213 | | 6,962,587 B2 | 11/2005 | Johnson et al. |
| 6,652,521 B2 | 11/2003 | Schulze | | 6,964,662 B2 | 11/2005 | Kidooka |
| 6,652,551 B1 | 11/2003 | Heiss | | 6,966,909 B2 | 11/2005 | Marshall et al. |
| 6,656,194 B1 | 12/2003 | Gannoe et al. | | 6,966,919 B2 | 11/2005 | Sixto, Jr. et al. |
| 6,663,641 B1 | 12/2003 | Kovac et al. | | 6,967,462 B1 | 11/2005 | Landis |
| 6,663,655 B2 * | 12/2003 | Ginn et al. ............... 606/213 | | 6,971,988 B2 | 12/2005 | Orban, III |
| 6,666,854 B1 | 12/2003 | Lange | | 6,972,017 B2 | 12/2005 | Smith et al. |
| 6,672,338 B1 | 1/2004 | Esashi et al. | | 6,974,411 B2 | 12/2005 | Belson |
| 6,673,058 B2 | 1/2004 | Snow | | 6,976,992 B2 | 12/2005 | Sachatello et al. |
| 6,673,087 B1 | 1/2004 | Chang et al. | | 6,984,203 B2 | 1/2006 | Tartaglia et al. |
| 6,679,882 B1 | 1/2004 | Kornerup | | 6,984,205 B2 | 1/2006 | Gazdzinski |
| 6,685,628 B2 | 2/2004 | Vu | | 6,986,774 B2 | 1/2006 | Middleman et al. |
| 6,685,724 B1 | 2/2004 | Haluck | | 6,988,987 B2 | 1/2006 | Ishikawa et al. |
| 6,692,445 B2 | 2/2004 | Roberts et al. | | 6,989,028 B2 | 1/2006 | Lashinski et al. |
| 6,692,462 B2 | 2/2004 | Mackenzie et al. | | 6,991,627 B2 | 1/2006 | Madhani et al. |
| 6,699,180 B2 | 3/2004 | Kobayashi | | 6,991,631 B2 | 1/2006 | Woloszko et al. |
| 6,699,256 B1 | 3/2004 | Logan et al. | | 6,994,708 B2 | 2/2006 | Manzo |
| 6,699,263 B2 | 3/2004 | Cope | | 6,997,931 B2 | 2/2006 | Sauer et al. |
| 6,706,018 B2 | 3/2004 | Westlund et al. | | 7,000,818 B2 | 2/2006 | Shelton, IV et al. |
| 6,708,066 B2 | 3/2004 | Herbst et al. | | 7,001,341 B2 | 2/2006 | Gellman et al. |
| 6,709,445 B2 | 3/2004 | Boebel et al. | | 7,008,375 B2 | 3/2006 | Weisel |
| 6,716,226 B2 | 4/2004 | Sixto, Jr. et al. | | 7,009,634 B2 | 3/2006 | Iddan et al. |
| 6,736,822 B2 | 5/2004 | McClellan et al. | | 7,010,340 B2 | 3/2006 | Scarantino et al. |
| 6,740,030 B2 | 5/2004 | Martone et al. | | 7,020,531 B1 | 3/2006 | Colliou et al. |

| Patent No. | Date | Inventor |
|---|---|---|
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 * | 8/2006 | Ginn ............................ 606/213 |
| 7,087,071 B2 | 8/2006 | Nicholas et al. |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,160,296 B2 | 1/2007 | Pearson et al. |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francere et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,335,220 B2 * | 2/2008 | Khosravi et al. ............... 606/213 |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,222 B2 | 7/2008 | Asakura |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 * | 11/2009 | Cragg et al. .................... 604/13 |
| 7,618,398 B2 | 11/2009 | Holman et al. |
| 7,621,936 B2 * | 11/2009 | Cragg et al. ................. 606/213 |
| 7,632,250 B2 | 12/2009 | Smith et al. |
| 7,635,373 B2 | 12/2009 | Ortiz |
| 7,637,903 B2 | 12/2009 | Lentz et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,674,259 B2 | 3/2010 | Shadduck |
| 7,678,043 B2 | 3/2010 | Gilad |
| 7,684,599 B2 | 3/2010 | Horn et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,736,374 B2 | 6/2010 | Vaughan et al. |

| Patent No. | Date | Name | | Pub. No. | Date | Name | |
|---|---|---|---|---|---|---|---|
| 7,744,615 B2 | 6/2010 | Couture | | 2003/0171651 A1 | 9/2003 | Page et al. | |
| 7,753,933 B2 * | 7/2010 | Ginn et al. | 606/213 | 2003/0176880 A1 | 9/2003 | Long et al. | |
| 7,758,577 B2 | 7/2010 | Nobis et al. | | 2003/0191497 A1 | 10/2003 | Cope | |
| 7,762,949 B2 | 7/2010 | Nakao | | 2003/0195560 A1 * | 10/2003 | Ginn | 606/213 |
| 7,762,998 B2 | 7/2010 | Birk et al. | | 2003/0195565 A1 | 10/2003 | Bonutti | |
| 7,763,012 B2 | 7/2010 | Petrick et al. | | 2003/0216611 A1 | 11/2003 | Vu | |
| 7,771,416 B2 | 8/2010 | Spivey et al. | | 2003/0216615 A1 | 11/2003 | Ouchi | |
| 7,780,683 B2 | 8/2010 | Roue et al. | | 2003/0220545 A1 | 11/2003 | Ouchi | |
| 7,780,691 B2 | 8/2010 | Stefanchik | | 2003/0225312 A1 | 12/2003 | Suzuki et al. | |
| 7,784,663 B2 | 8/2010 | Shelton, IV | | 2003/0225332 A1 | 12/2003 | Okada et al. | |
| 7,794,409 B2 | 9/2010 | Damarati | | 2003/0229269 A1 | 12/2003 | Humphrey | |
| 7,794,475 B2 | 9/2010 | Hess et al. | | 2003/0229371 A1 | 12/2003 | Whitworth | |
| 7,798,386 B2 | 9/2010 | Schall et al. | | 2003/0236549 A1 | 12/2003 | Bonadio et al. | |
| 7,828,186 B2 | 11/2010 | Wales | | 2004/0002683 A1 | 1/2004 | Nicholson et al. | |
| 7,837,615 B2 | 11/2010 | Le et al. | | 2004/0002735 A1 | 1/2004 | Lizardi et al. | |
| 7,842,028 B2 | 11/2010 | Lee | | 2004/0024414 A1 * | 2/2004 | Downing | 606/108 |
| 7,842,068 B2 * | 11/2010 | Ginn | 606/213 | 2004/0034369 A1 | 2/2004 | Sauer et al. | |
| 7,846,171 B2 | 12/2010 | Kullas et al. | | 2004/0054322 A1 | 3/2004 | Vargas | |
| 7,850,660 B2 | 12/2010 | Uth et al. | | 2004/0098007 A1 | 5/2004 | Heiss | |
| 7,857,183 B2 | 12/2010 | Shelton, IV | | 2004/0101456 A1 | 5/2004 | Kuroshima et al. | |
| 7,862,546 B2 | 1/2011 | Conlon et al. | | 2004/0104999 A1 | 6/2004 | Okada | |
| 7,867,216 B2 | 1/2011 | Wahr et al. | | 2004/0116948 A1 | 6/2004 | Sixto, Jr. et al. | |
| 7,892,220 B2 | 2/2011 | Faller et al. | | 2004/0127940 A1 * | 7/2004 | Ginn et al. | 606/213 |
| 7,896,887 B2 | 3/2011 | Rimbaugh et al. | | 2004/0133077 A1 | 7/2004 | Obenchain et al. | |
| 7,905,828 B2 | 3/2011 | Brock et al. | | 2004/0133089 A1 | 7/2004 | Kilcoyne et al. | |
| 7,909,809 B2 | 3/2011 | Scopton et al. | | 2004/0136779 A1 | 7/2004 | Bhaskar | |
| 7,914,513 B2 | 3/2011 | Voorhees, Jr. | | 2004/0138525 A1 | 7/2004 | Saadat et al. | |
| 7,918,869 B2 | 4/2011 | Saadat et al. | | 2004/0138527 A1 * | 7/2004 | Bonner et al. | 600/114 |
| 7,931,624 B2 | 4/2011 | Smith et al. | | 2004/0138529 A1 | 7/2004 | Wiltshire et al. | |
| 7,945,332 B2 | 5/2011 | Schechter | | 2004/0138587 A1 | 7/2004 | Lyons, IV | |
| 7,947,000 B2 | 5/2011 | Vargas et al. | | 2004/0161451 A1 | 8/2004 | Pierce et al. | |
| 7,955,298 B2 | 6/2011 | Carroll et al. | | 2004/0186350 A1 | 9/2004 | Brenneman et al. | |
| 7,963,975 B2 | 6/2011 | Criscuolo | | 2004/0193009 A1 | 9/2004 | Jaffe et al. | |
| 7,965,180 B2 | 6/2011 | Koyama | | 2004/0193146 A1 | 9/2004 | Lee et al. | |
| 7,967,808 B2 | 6/2011 | Fitzgerald et al. | | 2004/0193186 A1 | 9/2004 | Kortenbach et al. | |
| 7,969,473 B2 | 6/2011 | Kotoda | | 2004/0193188 A1 | 9/2004 | Francese | |
| 7,988,685 B2 | 8/2011 | Ziaie et al. | | 2004/0193189 A1 | 9/2004 | Kortenbach et al. | |
| 8,048,067 B2 | 11/2011 | Davalos et al. | | 2004/0193200 A1 | 9/2004 | Dworschak et al. | |
| 8,057,510 B2 * | 11/2011 | Ginn et al. | 606/213 | 2004/0199052 A1 | 10/2004 | Banik et al. | |
| 8,066,632 B2 | 11/2011 | Dario et al. | | 2004/0199159 A1 | 10/2004 | Lee et al. | |
| 8,075,587 B2 * | 12/2011 | Ginn | 606/213 | 2004/0206859 A1 | 10/2004 | Chong et al. | |
| 8,088,062 B2 | 1/2012 | Zwolinski | | 2004/0210245 A1 | 10/2004 | Erickson et al. | |
| 8,118,821 B2 | 2/2012 | Mouw | | 2004/0215058 A1 | 10/2004 | Zirps et al. | |
| 8,147,424 B2 * | 4/2012 | Kassab et al. | 600/564 | 2004/0225183 A1 | 11/2004 | Michlitsch et al. | |
| 2001/0023333 A1 * | 9/2001 | Wise et al. | 604/101.01 | 2004/0225186 A1 | 11/2004 | Horne, Jr. et al. | |
| 2001/0049497 A1 | 12/2001 | Kalloo et al. | | 2004/0230095 A1 | 11/2004 | Stefanchik et al. | |
| 2002/0022771 A1 | 2/2002 | Diokno et al. | | 2004/0230096 A1 | 11/2004 | Stefanchik et al. | |
| 2002/0022857 A1 | 2/2002 | Goldsteen et al. | | 2004/0230097 A1 | 11/2004 | Stefanchik et al. | |
| 2002/0023353 A1 | 2/2002 | Ting-Kung | | 2004/0230161 A1 | 11/2004 | Zeiner | |
| 2002/0029055 A1 | 3/2002 | Bonutti | | 2004/0249246 A1 | 12/2004 | Campos | |
| 2002/0042562 A1 | 4/2002 | Meron et al. | | 2004/0249367 A1 | 12/2004 | Saadat et al. | |
| 2002/0049439 A1 | 4/2002 | Mulier et al. | | 2004/0249394 A1 | 12/2004 | Morris et al. | |
| 2002/0068945 A1 | 6/2002 | Sixto, Jr. et al. | | 2004/0249443 A1 | 12/2004 | Shanley et al. | |
| 2002/0072768 A1 * | 6/2002 | Ginn | 606/213 | 2004/0254572 A1 | 12/2004 | McIntyre et al. | |
| 2002/0077657 A1 * | 6/2002 | Ginn et al. | 606/213 | 2005/0004515 A1 | 1/2005 | Hart et al. | |
| 2002/0078967 A1 | 6/2002 | Sixto, Jr. et al. | | 2005/0033265 A1 | 2/2005 | Engel et al. | |
| 2002/0082516 A1 | 6/2002 | Stefanchik | | 2005/0033277 A1 | 2/2005 | Clague et al. | |
| 2002/0091391 A1 | 7/2002 | Cole et al. | | 2005/0033319 A1 | 2/2005 | Gambale et al. | |
| 2002/0095164 A1 | 7/2002 | Andreas et al. | | 2005/0033333 A1 | 2/2005 | Smith et al. | |
| 2002/0107530 A1 | 8/2002 | Sauer et al. | | 2005/0043690 A1 | 2/2005 | Todd | |
| 2002/0133115 A1 | 9/2002 | Gordon et al. | | 2005/0049616 A1 | 3/2005 | Rivera et al. | |
| 2002/0138086 A1 | 9/2002 | Sixto, Jr. et al. | | 2005/0065397 A1 | 3/2005 | Saadat et al. | |
| 2002/0147456 A1 | 10/2002 | Diduch et al. | | 2005/0065517 A1 | 3/2005 | Chin | |
| 2002/0161378 A1 * | 10/2002 | Downing | 606/108 | 2005/0070754 A1 | 3/2005 | Nobis et al. | |
| 2002/0165592 A1 | 11/2002 | Glukhovsky et al. | | 2005/0070763 A1 | 3/2005 | Nobis et al. | |
| 2002/0183591 A1 | 12/2002 | Matsuura et al. | | 2005/0070764 A1 | 3/2005 | Nobis et al. | |
| 2003/0023255 A1 | 1/2003 | Miles et al. | | 2005/0080413 A1 | 4/2005 | Canady | |
| 2003/0032858 A1 * | 2/2003 | Ginn et al. | 600/36 | 2005/0085693 A1 | 4/2005 | Belson et al. | |
| 2003/0036679 A1 | 2/2003 | Kortenbach et al. | | 2005/0085832 A1 | 4/2005 | Sancoff et al. | |
| 2003/0069602 A1 | 4/2003 | Jacobs et al. | | 2005/0090837 A1 | 4/2005 | Sixto, Jr. et al. | |
| 2003/0083681 A1 | 5/2003 | Moutafis et al. | | 2005/0090838 A1 | 4/2005 | Sixto, Jr. et al. | |
| 2003/0114731 A1 | 6/2003 | Cadeddu et al. | | 2005/0101837 A1 | 5/2005 | Kalloo et al. | |
| 2003/0114732 A1 | 6/2003 | Webler et al. | | 2005/0101838 A1 | 5/2005 | Camillocci et al. | |
| 2003/0120257 A1 | 6/2003 | Houston et al. | | 2005/0101984 A1 | 5/2005 | Chanduszko et al. | |
| 2003/0124009 A1 | 7/2003 | Ravi et al. | | 2005/0107663 A1 | 5/2005 | Saadat et al. | |
| 2003/0130564 A1 | 7/2003 | Martone et al. | | 2005/0107664 A1 | 5/2005 | Kalloo et al. | |
| 2003/0130656 A1 | 7/2003 | Levin | | 2005/0110881 A1 | 5/2005 | Glukhovsky et al. | |
| 2003/0158521 A1 | 8/2003 | Ameri | | 2005/0113847 A1 | 5/2005 | Gadberry et al. | |
| 2003/0167062 A1 | 9/2003 | Gambale et al. | | 2005/0119613 A1 | 6/2005 | Moenning et al. | |

| | | | | | |
|---|---|---|---|---|---|
| 2005/0124855 A1 | 6/2005 | Jaffe et al. | 2006/0135984 A1 | 6/2006 | Kramer et al. |
| 2005/0125010 A1 | 6/2005 | Smith et al. | 2006/0142644 A1 | 6/2006 | Mulac et al. |
| 2005/0131279 A1 | 6/2005 | Boulais et al. | 2006/0142652 A1 | 6/2006 | Keenan |
| 2005/0131457 A1 | 6/2005 | Douglas et al. | 2006/0142790 A1 | 6/2006 | Gertner |
| 2005/0137454 A1 | 6/2005 | Saadat et al. | 2006/0142798 A1 | 6/2006 | Holman et al. |
| 2005/0143647 A1 | 6/2005 | Minai et al. | 2006/0149131 A1 | 7/2006 | Or |
| 2005/0143690 A1 | 6/2005 | High | 2006/0149132 A1 | 7/2006 | Iddan |
| 2005/0143774 A1 | 6/2005 | Polo | 2006/0149135 A1 | 7/2006 | Paz |
| 2005/0143803 A1 | 6/2005 | Watson et al. | 2006/0161190 A1 | 7/2006 | Gadberry et al. |
| 2005/0149087 A1 | 7/2005 | Ahlberg et al. | 2006/0167416 A1 | 7/2006 | Mathis et al. |
| 2005/0149096 A1 | 7/2005 | Hilal et al. | 2006/0167482 A1 | 7/2006 | Swain et al. |
| 2005/0159648 A1 | 7/2005 | Freed | 2006/0178560 A1 | 8/2006 | Saadat et al. |
| 2005/0165272 A1 | 7/2005 | Okada et al. | 2006/0183975 A1 | 8/2006 | Saadat et al. |
| 2005/0165378 A1 | 7/2005 | Heinrich et al. | 2006/0184161 A1 | 8/2006 | Maahs et al. |
| 2005/0165411 A1 | 7/2005 | Orban, III | 2006/0189844 A1 | 8/2006 | Tien |
| 2005/0165429 A1 | 7/2005 | Douglas et al. | 2006/0189845 A1 | 8/2006 | Maahs et al. |
| 2005/0182429 A1 | 8/2005 | Yamanouchi | 2006/0190027 A1 | 8/2006 | Downey |
| 2005/0192478 A1 | 9/2005 | Williams et al. | 2006/0195084 A1 | 8/2006 | Slater |
| 2005/0192598 A1 | 9/2005 | Johnson et al. | 2006/0200005 A1 | 9/2006 | Bjork et al. |
| 2005/0192602 A1 | 9/2005 | Manzo | 2006/0200121 A1 | 9/2006 | Mowery |
| 2005/0192654 A1 | 9/2005 | Chanduszko et al. | 2006/0200169 A1 | 9/2006 | Sniffin |
| 2005/0209624 A1 | 9/2005 | Vijay | 2006/0200170 A1 | 9/2006 | Aranyi |
| 2005/0215858 A1 | 9/2005 | Vail, III | 2006/0200199 A1 | 9/2006 | Bonutti et al. |
| 2005/0216050 A1 | 9/2005 | Sepetka et al. | 2006/0217665 A1 | 9/2006 | Prosek |
| 2005/0228406 A1 | 10/2005 | Bose | 2006/0217697 A1 | 9/2006 | Lau et al. |
| 2005/0234297 A1 | 10/2005 | Devierre et al. | 2006/0217742 A1 | 9/2006 | Messerly et al. |
| 2005/0250983 A1 | 11/2005 | Tremaglio et al. | 2006/0217743 A1 | 9/2006 | Messerly et al. |
| 2005/0250990 A1 | 11/2005 | Le et al. | 2006/0229639 A1 | 10/2006 | Whitfield |
| 2005/0250993 A1 | 11/2005 | Jaeger | 2006/0229640 A1 | 10/2006 | Whitfield |
| 2005/0251166 A1 | 11/2005 | Vaughan et al. | 2006/0237022 A1 | 10/2006 | Chen et al. |
| 2005/0251176 A1 | 11/2005 | Swanstrom et al. | 2006/0237023 A1 | 10/2006 | Cox et al. |
| 2005/0261674 A1 | 11/2005 | Nobis et al. | 2006/0241570 A1 | 10/2006 | Wilk |
| 2005/0267492 A1 | 12/2005 | Poncet et al. | 2006/0247576 A1 | 11/2006 | Poncet |
| 2005/0272975 A1 | 12/2005 | McWeeney et al. | 2006/0247673 A1 | 11/2006 | Voegele et al. |
| 2005/0272977 A1 | 12/2005 | Saadat et al. | 2006/0253004 A1 | 11/2006 | Frisch et al. |
| 2005/0273084 A1 | 12/2005 | Hinman et al. | 2006/0253039 A1 | 11/2006 | McKenna et al. |
| 2005/0273137 A1 * | 12/2005 | Ginn ............................ 606/213 | 2006/0258907 A1 | 11/2006 | Stefanchik et al. |
| 2005/0274935 A1 | 12/2005 | Nelson | 2006/0258908 A1 | 11/2006 | Stefanchik et al. |
| 2005/0277945 A1 | 12/2005 | Saadat et al. | 2006/0258910 A1 | 11/2006 | Stefanchik et al. |
| 2005/0277951 A1 | 12/2005 | Smith et al. | 2006/0258954 A1 | 11/2006 | Timberlake et al. |
| 2005/0277952 A1 | 12/2005 | Arp et al. | 2006/0258955 A1 | 11/2006 | Hoffman et al. |
| 2005/0277954 A1 | 12/2005 | Smith et al. | 2006/0259010 A1 | 11/2006 | Stefanchik et al. |
| 2005/0277955 A1 | 12/2005 | Palmer et al. | 2006/0264752 A1 | 11/2006 | Rubinsky et al. |
| 2005/0277956 A1 | 12/2005 | Francese et al. | 2006/0264904 A1 | 11/2006 | Kerby et al. |
| 2005/0277957 A1 | 12/2005 | Kuhns et al. | 2006/0264930 A1 | 11/2006 | Nishimura |
| 2005/0283118 A1 | 12/2005 | Uth et al. | 2006/0270902 A1 | 11/2006 | Igarashi et al. |
| 2005/0283119 A1 | 12/2005 | Uth et al. | 2006/0271042 A1 | 11/2006 | Latterell et al. |
| 2005/0288555 A1 | 12/2005 | Binmoeller | 2006/0271102 A1 | 11/2006 | Bosshard et al. |
| 2006/0004406 A1 | 1/2006 | Wehrstein et al. | 2006/0276835 A1 | 12/2006 | Uchida |
| 2006/0004409 A1 | 1/2006 | Nobis et al. | 2006/0281970 A1 | 12/2006 | Stokes et al. |
| 2006/0004410 A1 | 1/2006 | Nobis et al. | 2006/0282106 A1 | 12/2006 | Cole et al. |
| 2006/0015009 A1 | 1/2006 | Jaffe et al. | 2006/0285732 A1 | 12/2006 | Horn et al. |
| 2006/0020167 A1 | 1/2006 | Sitzmann | 2006/0287644 A1 | 12/2006 | Inganas et al. |
| 2006/0020247 A1 | 1/2006 | Kagan et al. | 2006/0287666 A1 | 12/2006 | Saadat et al. |
| 2006/0025654 A1 | 2/2006 | Suzuki et al. | 2006/0293626 A1 | 12/2006 | Byrum et al. |
| 2006/0025781 A1 | 2/2006 | Young et al. | 2007/0002135 A1 | 1/2007 | Glukhovsky |
| 2006/0025812 A1 | 2/2006 | Shelton, IV | 2007/0005019 A1 | 1/2007 | Okishige |
| 2006/0025819 A1 | 2/2006 | Nobis et al. | 2007/0010801 A1 | 1/2007 | Chen et al. |
| 2006/0036267 A1 | 2/2006 | Saadat et al. | 2007/0015965 A1 | 1/2007 | Cox et al. |
| 2006/0041188 A1 | 2/2006 | Dirusso et al. | 2007/0016255 A1 | 1/2007 | Korb et al. |
| 2006/0058582 A1 | 3/2006 | Maahs et al. | 2007/0032700 A1 | 2/2007 | Fowler et al. |
| 2006/0058776 A1 | 3/2006 | Bilsbury | 2007/0032701 A1 | 2/2007 | Fowler et al. |
| 2006/0069396 A1 | 3/2006 | Meade et al. | 2007/0043261 A1 | 2/2007 | Watanabe et al. |
| 2006/0069424 A1 | 3/2006 | Acosta et al. | 2007/0043345 A1 | 2/2007 | Davalos et al. |
| 2006/0069425 A1 | 3/2006 | Hillis et al. | 2007/0049800 A1 | 3/2007 | Boulais |
| 2006/0069429 A1 | 3/2006 | Spence et al. | 2007/0049902 A1 | 3/2007 | Griffin et al. |
| 2006/0074413 A1 | 4/2006 | Behzadian | 2007/0051375 A1 | 3/2007 | Milliman |
| 2006/0079890 A1 | 4/2006 | Guerra | 2007/0060880 A1 | 3/2007 | Gregorich et al. |
| 2006/0089528 A1 | 4/2006 | Tartaglia et al. | 2007/0067017 A1 | 3/2007 | Trapp |
| 2006/0095031 A1 | 5/2006 | Ormsby | 2007/0073102 A1 | 3/2007 | Matsuno et al. |
| 2006/0095060 A1 | 5/2006 | Mayenberger et al. | 2007/0073269 A1 | 3/2007 | Becker |
| 2006/0100687 A1 | 5/2006 | Fahey et al. | 2007/0079924 A1 | 4/2007 | Saadat et al. |
| 2006/0106423 A1 | 5/2006 | Weisel et al. | 2007/0088370 A1 | 4/2007 | Kahle et al. |
| 2006/0111209 A1 | 5/2006 | Hinman et al. | 2007/0100375 A1 | 5/2007 | Mikkaichi et al. |
| 2006/0111210 A1 | 5/2006 | Hinman et al. | 2007/0100376 A1 | 5/2007 | Mikkaichi et al. |
| 2006/0111704 A1 | 5/2006 | Brenneman et al. | 2007/0106118 A1 | 5/2007 | Moriyama |
| 2006/0129166 A1 | 6/2006 | Lavelle | 2007/0112251 A1 | 5/2007 | Nakhuda |
| 2006/0135962 A1 | 6/2006 | Kick et al. | 2007/0112331 A1 | 5/2007 | Weber et al. |
| 2006/0135971 A1 | 6/2006 | Swanstrom et al. | 2007/0112342 A1 | 5/2007 | Pearson et al. |

| | | | | | | |
|---|---|---|---|---|---|---|
| 2007/0112383 A1 | 5/2007 | Conlon et al. | | 2008/0139882 A1 | 6/2008 | Fujimori |
| 2007/0112384 A1 | 5/2007 | Conlon et al. | | 2008/0140071 A1 | 6/2008 | Vegesna |
| 2007/0112385 A1 | 5/2007 | Conlon | | 2008/0147113 A1 | 6/2008 | Nobis et al. |
| 2007/0112417 A1 | 5/2007 | Shanley et al. | | 2008/0171907 A1 | 7/2008 | Long et al. |
| 2007/0112425 A1 | 5/2007 | Schaller et al. | | 2008/0177135 A1 | 7/2008 | Muyari et al. |
| 2007/0118115 A1 | 5/2007 | Artale et al. | | 2008/0188710 A1 | 8/2008 | Segawa et al. |
| 2007/0123840 A1 | 5/2007 | Cox | | 2008/0188868 A1 | 8/2008 | Weitzner et al. |
| 2007/0129605 A1 | 6/2007 | Schaaf | | 2008/0200755 A1 | 8/2008 | Bakos |
| 2007/0129719 A1 | 6/2007 | Kendale et al. | | 2008/0200762 A1 | 8/2008 | Stokes et al. |
| 2007/0129760 A1 | 6/2007 | Demarais et al. | | 2008/0200911 A1 | 8/2008 | Long |
| 2007/0135709 A1 | 6/2007 | Rioux et al. | | 2008/0200912 A1 | 8/2008 | Long |
| 2007/0135803 A1 | 6/2007 | Belson | | 2008/0200933 A1 | 8/2008 | Bakos et al. |
| 2007/0142706 A1 | 6/2007 | Matsui et al. | | 2008/0200934 A1 | 8/2008 | Fox |
| 2007/0142780 A1 | 6/2007 | Van Lue | | 2008/0208213 A1 | 8/2008 | Benjamin et al. |
| 2007/0154460 A1 | 7/2007 | Kraft et al. | | 2008/0221587 A1 | 9/2008 | Schwartz |
| 2007/0156028 A1 | 7/2007 | Van Lue et al. | | 2008/0221619 A1 | 9/2008 | Spivey et al. |
| 2007/0156127 A1 | 7/2007 | Rioux et al. | | 2008/0228213 A1 | 9/2008 | Blakeney et al. |
| 2007/0161855 A1 | 7/2007 | Mikkaichi et al. | | 2008/0230972 A1 | 9/2008 | Ganley |
| 2007/0162101 A1 | 7/2007 | Burgermeister et al. | | 2008/0234696 A1 | 9/2008 | Taylor et al. |
| 2007/0167901 A1* | 7/2007 | Herrig et al. ............ 604/6.16 | | 2008/0243106 A1 | 10/2008 | Coe et al. |
| 2007/0173691 A1 | 7/2007 | Yokoi et al. | | 2008/0243148 A1 | 10/2008 | Mikkaichi et al. |
| 2007/0173869 A1 | 7/2007 | Gannoe et al. | | 2008/0243176 A1 | 10/2008 | Weitzner et al. |
| 2007/0173870 A2 | 7/2007 | Zacharias | | 2008/0249567 A1* | 10/2008 | Kaplan ................ 606/232 |
| 2007/0173872 A1 | 7/2007 | Neuenfeldt | | 2008/0262513 A1 | 10/2008 | Stahler et al. |
| 2007/0179525 A1 | 8/2007 | Frecker et al. | | 2008/0262540 A1 | 10/2008 | Bangera et al. |
| 2007/0179530 A1 | 8/2007 | Tieu et al. | | 2008/0269782 A1 | 10/2008 | Stefanchik et al. |
| 2007/0197865 A1 | 8/2007 | Miyake et al. | | 2008/0269783 A1 | 10/2008 | Griffith |
| 2007/0198057 A1 | 8/2007 | Gelbart et al. | | 2008/0275474 A1 | 11/2008 | Martin et al. |
| 2007/0203398 A1 | 8/2007 | Bonadio et al. | | 2008/0275475 A1 | 11/2008 | Schwemberger et al. |
| 2007/0203487 A1 | 8/2007 | Sugita | | 2008/0287737 A1 | 11/2008 | Dejima |
| 2007/0208336 A1 | 9/2007 | Kim et al. | | 2008/0287983 A1 | 11/2008 | Smith et al. |
| 2007/0208364 A1 | 9/2007 | Smith et al. | | 2008/0300461 A1 | 12/2008 | Shaw et al. |
| 2007/0213754 A1 | 9/2007 | Mikkaichi et al. | | 2008/0300547 A1 | 12/2008 | Bakos |
| 2007/0225554 A1 | 9/2007 | Maseda et al. | | 2008/0309758 A1 | 12/2008 | Karasawa et al. |
| 2007/0233040 A1 | 10/2007 | Macnamara et al. | | 2008/0312496 A1 | 12/2008 | Zwolinski |
| 2007/0244358 A1 | 10/2007 | Lee | | 2008/0312499 A1 | 12/2008 | Handa et al. |
| 2007/0250038 A1 | 10/2007 | Boulais | | 2008/0312500 A1 | 12/2008 | Asada et al. |
| 2007/0250057 A1 | 10/2007 | Nobis et al. | | 2008/0312506 A1 | 12/2008 | Spivey et al. |
| 2007/0255096 A1 | 11/2007 | Stefanchik et al. | | 2008/0319436 A1 | 12/2008 | Daniel et al. |
| 2007/0255100 A1 | 11/2007 | Barlow et al. | | 2008/0319439 A1 | 12/2008 | Ootsubu |
| 2007/0255273 A1 | 11/2007 | Fernandez et al. | | 2009/0054728 A1 | 2/2009 | Trusty |
| 2007/0255303 A1 | 11/2007 | Bakos et al. | | 2009/0062788 A1 | 3/2009 | Long et al. |
| 2007/0255306 A1 | 11/2007 | Conlon et al. | | 2009/0062792 A1 | 3/2009 | Vakharia et al. |
| 2007/0260112 A1 | 11/2007 | Rahmani | | 2009/0062795 A1 | 3/2009 | Vakharia et al. |
| 2007/0260117 A1 | 11/2007 | Zwolinski et al. | | 2009/0069634 A1 | 3/2009 | Larkin |
| 2007/0260121 A1 | 11/2007 | Bakos et al. | | 2009/0076499 A1 | 3/2009 | Azure |
| 2007/0260242 A1 | 11/2007 | Dycus et al. | | 2009/0078736 A1 | 3/2009 | Van Lue |
| 2007/0260273 A1 | 11/2007 | Cropper et al. | | 2009/0082776 A1 | 3/2009 | Cresina |
| 2007/0270629 A1 | 11/2007 | Charles | | 2009/0082779 A1 | 3/2009 | Nakao |
| 2007/0270889 A1 | 11/2007 | Conlon et al. | | 2009/0112059 A1 | 4/2009 | Nobis |
| 2007/0270895 A1 | 11/2007 | Nobis et al. | | 2009/0112063 A1 | 4/2009 | Bakos et al. |
| 2007/0270907 A1 | 11/2007 | Stokes et al. | | 2009/0125042 A1 | 5/2009 | Mouw |
| 2007/0282371 A1 | 12/2007 | Lee et al. | | 2009/0131751 A1 | 5/2009 | Spivey et al. |
| 2007/0293727 A1 | 12/2007 | Goldfarb et al. | | 2009/0131932 A1 | 5/2009 | Vakharia et al. |
| 2007/0299387 A1 | 12/2007 | Williams et al. | | 2009/0131933 A1 | 5/2009 | Ghabrial et al. |
| 2008/0004650 A1 | 1/2008 | George | | 2009/0143639 A1 | 6/2009 | Stark |
| 2008/0015409 A1 | 1/2008 | Barlow et al. | | 2009/0143649 A1 | 6/2009 | Rossi |
| 2008/0015413 A1 | 1/2008 | Barlow et al. | | 2009/0143794 A1 | 6/2009 | Conlon et al. |
| 2008/0015552 A1 | 1/2008 | Doyle et al. | | 2009/0143818 A1 | 6/2009 | Faller et al. |
| 2008/0021416 A1 | 1/2008 | Arai et al. | | 2009/0149710 A1 | 6/2009 | Stefanchik et al. |
| 2008/0022927 A1 | 1/2008 | Zhang et al. | | 2009/0177031 A1 | 7/2009 | Surti et al. |
| 2008/0027387 A1 | 1/2008 | Grabinsky | | 2009/0177219 A1 | 7/2009 | Conlon |
| 2008/0033451 A1 | 2/2008 | Rieber et al. | | 2009/0182332 A1 | 7/2009 | Long et al. |
| 2008/0051629 A1 | 2/2008 | Sugiyama et al. | | 2009/0192344 A1 | 7/2009 | Bakos et al. |
| 2008/0051735 A1 | 2/2008 | Measamer et al. | | 2009/0192534 A1 | 7/2009 | Ortiz et al. |
| 2008/0058586 A1 | 3/2008 | Karpiel | | 2009/0198231 A1 | 8/2009 | Esser et al. |
| 2008/0058854 A1 | 3/2008 | Kieturakis et al. | | 2009/0198253 A1 | 8/2009 | Omori |
| 2008/0065169 A1 | 3/2008 | Colliou et al. | | 2009/0210000 A1* | 8/2009 | Sullivan et al. ............ 606/213 |
| 2008/0071264 A1 | 3/2008 | Azure | | 2009/0216248 A1 | 8/2009 | Uenohara et al. |
| 2008/0086172 A1 | 4/2008 | Martin et al. | | 2009/0227828 A1 | 9/2009 | Swain et al. |
| 2008/0097159 A1 | 4/2008 | Ishiguro | | 2009/0248055 A1 | 10/2009 | Spivey et al. |
| 2008/0097472 A1 | 4/2008 | Agmon et al. | | 2009/0269317 A1 | 10/2009 | Davalos |
| 2008/0097483 A1 | 4/2008 | Ortiz et al. | | 2009/0281559 A1 | 11/2009 | Swain et al. |
| 2008/0103527 A1 | 5/2008 | Martin et al. | | 2009/0287206 A1 | 11/2009 | Jun |
| 2008/0114384 A1 | 5/2008 | Chang et al. | | 2009/0287236 A1 | 11/2009 | Bakos et al. |
| 2008/0119870 A1 | 5/2008 | Williams | | 2009/0292164 A1 | 11/2009 | Yamatani |
| 2008/0119891 A1 | 5/2008 | Miles et al. | | 2009/0299135 A1 | 12/2009 | Spivey |
| 2008/0125796 A1 | 5/2008 | Graham | | 2009/0299143 A1 | 12/2009 | Conlon et al. |
| 2008/0132892 A1 | 6/2008 | Lunsford et al. | | 2009/0299362 A1 | 12/2009 | Long et al. |

| | | |
|---|---|---|
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326332 A1 | 12/2009 | Carter |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0056864 A1 | 3/2010 | Lee |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0261994 A1 | 10/2010 | Davalos et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0106221 A1 | 5/2011 | Neal, II et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0193948 A1 | 8/2011 | Amling et al. |
| 2011/0245619 A1 | 10/2011 | Holcomb |
| 2011/0285488 A1 | 11/2011 | Scott et al. |
| 2011/0306971 A1 | 12/2011 | Long |
| 2012/0004502 A1 | 1/2012 | Weitzner et al. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0116155 A1 | 5/2012 | Trusty |
| 2012/0179148 A1 | 7/2012 | Conlon |
| 2012/0191075 A1 | 7/2012 | Trusty |
| 2012/0191076 A1 | 7/2012 | Voegele et al. |
| 2012/0220998 A1 | 8/2012 | Long et al. |
| 2012/0220999 A1 | 8/2012 | Long |
| 2012/0221002 A1 | 8/2012 | Long et al. |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 1493397 B1 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A | 3/2003 |
| JP | 2003-235852 A | 8/2003 |
| JP | 2004-33525 A | 2/2004 |

| | | | |
|---|---|---|---|
| JP | 2004-065745 A | 3/2004 | |
| JP | 2005-121947 A | 5/2005 | |
| JP | 2005-261514 A | 9/2005 | |
| JP | 2006297005 A | 11/2006 | |
| NL | 1021295 C2 | 2/2004 | |
| SU | 194230 | 5/1967 | |
| SU | 980703 | 12/1982 | |
| WO | WO 84/01707 A1 | 5/1984 | |
| WO | WO 92/13494 A1 | 8/1992 | |
| WO | WO 93/10850 A1 | 6/1993 | |
| WO | WO 93/20760 A1 | 10/1993 | |
| WO | WO 93/20765 A1 | 10/1993 | |
| WO | WO 95/09666 A1 | 4/1995 | |
| WO | WO 96/22056 A1 | 7/1996 | |
| WO | WO 96/27331 A1 | 9/1996 | |
| WO | WO 96/39946 A1 | 12/1996 | |
| WO | WO 97/12557 A1 | 4/1997 | |
| WO | WO 98/01080 A1 | 1/1998 | |
| WO | WO 99/00060 A1 | 1/1999 | |
| WO | WO 99/09919 A1 | 3/1999 | |
| WO | WO 99/17661 A1 | 4/1999 | |
| WO | WO 99/30622 A2 | 6/1999 | |
| WO | WO 00/35358 A1 | 6/2000 | |
| WO | WO 01/10319 A1 | 2/2001 | |
| WO | WO 01/26708 A1 | 4/2001 | |
| WO | WO 01/41627 A2 | 6/2001 | |
| WO | WO 01/58360 A2 | 8/2001 | |
| WO | WO 02/11621 A1 | 2/2002 | |
| WO | WO 02/34122 A2 | 5/2002 | |
| WO | WO 02/094082 A2 | 11/2002 | |
| WO | WO 03/045260 A1 | 6/2003 | |
| WO | WO 03/047684 A2 | 6/2003 | |
| WO | WO 03/059412 A2 | 7/2003 | |
| WO | WO 03/078721 A2 | 9/2003 | |
| WO | WO 03/081761 A2 | 10/2003 | |
| WO | WO 03/082129 A2 | 10/2003 | |
| WO | WO 2004/006789 A1 | 1/2004 | |
| WO | WO 2004/028613 A2 | 4/2004 | |
| WO | WO 2004/037123 A1 | 5/2004 | |
| WO | WO 2004/037149 A1 | 5/2004 | |
| WO | WO 2004/052221 A1 | 6/2004 | |
| WO | WO 2004/086984 A1 | 10/2004 | |
| WO | WO 2005/009211 A2 | 2/2005 | |
| WO | WO 2005/018467 A2 | 3/2005 | |
| WO | WO 2005/037088 A2 | 4/2005 | |
| WO | WO 2005/048827 A1 | 6/2005 | |
| WO | WO 2005/065284 A2 | 7/2005 | |
| WO | WO 2005/097019 A2 | 10/2005 | |
| WO | WO 2005/097234 A2 | 10/2005 | |
| WO | WO 2005/112810 A2 | 12/2005 | |
| WO | WO 2005/120363 A1 | 12/2005 | |
| WO | WO 2005/122866 A1 | 12/2005 | |
| WO | WO 2006/007399 A1 | 1/2006 | |
| WO | WO 2006/012630 A2 | 2/2006 | |
| WO | WO 2006/040109 A1 | 4/2006 | |
| WO | WO 2006/041881 A2 | 4/2006 | |
| WO | WO 2006/060405 A2 | 6/2006 | |
| WO | WO 2006/110733 A2 | 10/2006 | |
| WO | WO 2006/113216 A2 | 10/2006 | |
| WO | WO 2007/013059 A2 | 2/2007 | |
| WO | WO 2007/014063 A2 | 2/2007 | |
| WO | WO 2007/048085 A2 | 4/2007 | |
| WO | WO 2007/063550 A2 | 6/2007 | |
| WO | WO 2007/100067 A1 | 9/2007 | |
| WO | WO 2007/109171 A2 | 9/2007 | |
| WO | WO 2008/005433 A1 | 1/2008 | |
| WO | WO 2008/033356 A2 | 3/2008 | |
| WO | WO 2008/041225 A2 | 4/2008 | |
| WO | WO 2008/076337 A1 | 6/2008 | |
| WO | WO 2008/076800 A2 | 6/2008 | |
| WO | WO 2008/079440 A2 | 7/2008 | |
| WO | WO 2008/101075 A2 | 8/2008 | |
| WO | WO 2008/102154 A2 | 8/2008 | |
| WO | WO 2008/108863 A2 | 9/2008 | |
| WO | WO 2008/151237 A1 | 12/2008 | |
| WO | WO 2009/021030 A1 | 2/2009 | |
| WO | WO 2009/027065 A1 | 3/2009 | |
| WO | WO 2009/029065 A1 | 3/2009 | |
| WO | WO 2009/032623 A2 | 3/2009 | |
| WO | WO 2009/121017 A1 | 10/2009 | |
| WO | WO 2010/027688 A1 | 3/2010 | |
| WO | WO 2010/056716 A2 | 5/2010 | |
| WO | WO 2010/080974 A1 | 7/2010 | |
| WO | WO 2010/088481 A1 | 8/2010 | |

OTHER PUBLICATIONS

F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: lmpr. D'Achard, 1826; 1:127-31. (with English translation).
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRe1Id=1000.1003&method=D . . . , accessed Jul. 18, 2008 (4 pages).
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/060,601, filed Apr. 1, 2008.
U.S. Appl. No. 11/952,475, filed Dec. 7, 2007.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
Written Opinion for PCT/US2008/081736, Feb. 3, 2009 (6 pages).
International Preliminary Report on Patentability for PCT/US2008/081736, mailed May 14, 2010 (7 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).
D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked Ni-Ti," Engineering Aspects of Shape Memory Alloys, pp. 414-419 (1990).
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
International Search Report for PCT/US2008/081736, Feb. 3, 2009 (9 pages).
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (publication date unknown).

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
"Z-Offset Technique Used in the Introduction of Trocar During Laparoscopic Surgery," M.S. Hershey NOTES Presentation to EES NOTES Development Team, Sep. 27, 2007.
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
U.S. Appl. No. 11/274,352, filed Nov. 15, 2005.

U.S. Appl. No. 11/274,354, filed Nov. 15, 2005.
U.S. Appl. No. 11/274,358, filed Nov. 15, 2005.
U.S. Appl. No. 11/437,440, filed May 19, 2006.
U.S. Appl. No. 11/437,864, filed May 19, 2006.
U.S. Appl. No. 11/610,803, filed Dec. 14, 2006.
U.S. Appl. No. 11/706,460, filed Feb. 15, 2007.
U.S. Appl. No. 11/706,591, filed Feb. 15, 2007.
U.S. Appl. No. 11/706,685, filed Feb. 15, 2007.
U.S. Appl. No. 11/706,766, filed Feb. 15, 2007.
U.S. Appl. No. 11/706,811, filed Feb. 15, 2007.
U.S. Appl. No. 11/707,831, filed Feb. 16, 2007.
U.S. Appl. No. 11/715,710, filed Mar. 8, 2007.
U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818 filed Mar. 15, 2012.

* cited by examiner

DETACHABLE DISTAL OVERTUBE SECTION AND METHODS FOR FORMING A SEALABLE OPENING IN THE WALL OF AN ORGAN

FIELD OF THE INVENTION

The present invention relates, in general, to surgical devices and methods of use and, more particularly, to devices and methods for forming a sealable passageway through the wall of an organ.

BACKGROUND OF THE INVENTION

Access to the abdominal cavity may, from time to time, be required for diagnostic and therapeutic endeavors for a variety of medical and surgical diseases. Historically, abdominal access has required a formal laparotomy to provide adequate exposure. Such procedures which require incisions to be made in the abdomen are not particularly well-suited for patients that may have extensive abdominal scarring from previous procedures, those persons who are morbidly obese, those individuals with abdominal wall infection, and those patients with diminished abdominal wall integrity, such as patients with burns and skin grafting. Other patients simply do not want to have a scar if it can be avoided.

Minimally invasive procedures are desirable because such procedures can reduce pain and provide relatively quick recovery times as compared with conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall.

Still less invasive treatments include those that are performed through insertion of an endoscope through a natural body orifice to a treatment region. Examples of this approach include, but are not limited to, cystoscopy, hysteroscopy, esophagogastroduodenoscopy, and colonoscopy. Many of these procedures employ the use of a flexible endoscope during the procedure. Flexible endoscopes often have a flexible, steerable articulating section near the distal end that can be controlled by the user by utilizing controls at the proximal end. Minimally invasive therapeutic procedures to treat diseased tissue by introducing medical instruments to a tissue treatment region through a natural opening of the patient are known as Natural Orifice Translumenal Endoscopic Surgery (NOTES)™.

Some flexible endoscopes are relatively small (1 mm to 3 mm in diameter), and may have no integral accessory channel (also called biopsy channels or working channels). Other flexible endoscopes, including gastroscopes and colonoscopes, have integral working channels having a diameter of about 2.0 to 3.5 mm for the purpose of introducing and removing medical devices and other accessory devices to perform diagnosis or therapy within the patient.

Some surgical applications require the endoscope to be passed through the wall of an organ to gain access to a body cavity. After the procedure is completed within the body cavity and the endoscope is removed, the opening may need to be closed. However, in some situations, it may become necessary to reenter the body cavity through the organ wall after the original opening has been permanently closed. In those instances, the surgeon must reopen the original opening or form a new opening through the organ wall.

Over the years, a variety of different guide tubes and overtubes have been developed for guiding endoscopic surgical instruments into position. However, such instruments generally lack the ability to form a sealable opening through an organ wall through which surgical instruments such as endoscopes, etc. may be passed.

Consequently a need exists for an overtube device that can be used to facilitate the entry and guidance of surgical instruments through a natural orifice in the body and also be employed to form a sealable opening through the wall of an organ that can be reopened if necessary.

The foregoing discussion is intended only to illustrate some of the shortcomings present in the field of the invention at the time, and should not be taken as a disavowal of claim scope.

SUMMARY

In one aspect of the invention, there is provided an overtube for use with an endoscopic surgical instrument. In various embodiments, the overtube may comprise a hollow tubular member that has a proximal end and a distal end. An implantable tip may be detachably affixed to the distal end of the hollow tubular member. The implantable tip may have a lumen extending therethrough. A plug member may be sealingly attachable within the implantable tip to selectively seal off the lumen.

In another general aspect of various embodiments of the present invention, there is provided a surgical method for forming a sealable opening through the wall of an organ located in a body. The method may include providing a hollow tubular member that has a proximal end and a distal end wherein the distal end has an implantable tip detachably affixed thereto and wherein the implantable tip has a lumen extending therethrough. The method may further include supporting the implantable tip adjacent the organ wall and forming a hole through the organ wall. The method may also include implanting the implantable tip in the hole in the organ wall and sealing off the lumen in the implantable tip. Thereafter the hollow tubular member may be detached from the implantable tip.

In still another general aspect of various embodiments of the present invention, there is provided an overtube for use with an endoscopic surgical instrument. In various embodiments, the overtube may include, for example, a hollow tubular member that has a proximal end and a distal end. The overtube may further include an implantable tip that is detachably affixed to the distal end of the hollow tubular member. The implantable tip may have a substantially frustoconically shaped distal end and at least one retention barb formed thereon. A plug member may be sealingly attachable within the implantable tip to selectively seal off a lumen extending through the implantable tip.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain various principles of the present invention.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

It will be appreciated that the terms "proximal" and "distal" are used herein with reference to a clinician manipulating an end of the instrument 20 that protrudes out of the natural orifice. The term "proximal" referring to the portion closest to the clinician and the term "distal" referring to the portion located away from the clinician. It will be further appreciated that, for convenience and clarity, spatial terms such as "vertical", "horizontal", "up" and "down" may be used herein with respect to the drawings. However, surgical instruments are used in many orientations and positions, and these terms are not intended to be limiting and/or absolute.

The present invention generally relates to various overtube arrangements and methods for use in forming an opening through the wall of an organ. Some embodiments may also be equipped with a seal or a plug for selectively plugging the opening. Those of ordinary skill in the art will appreciate that the various overtube arrangements and methods of the present invention may be effectively used in connection with various types of endoscopes and other surgical instruments without departing from the spirit and scope of the present invention.

Figure 1:
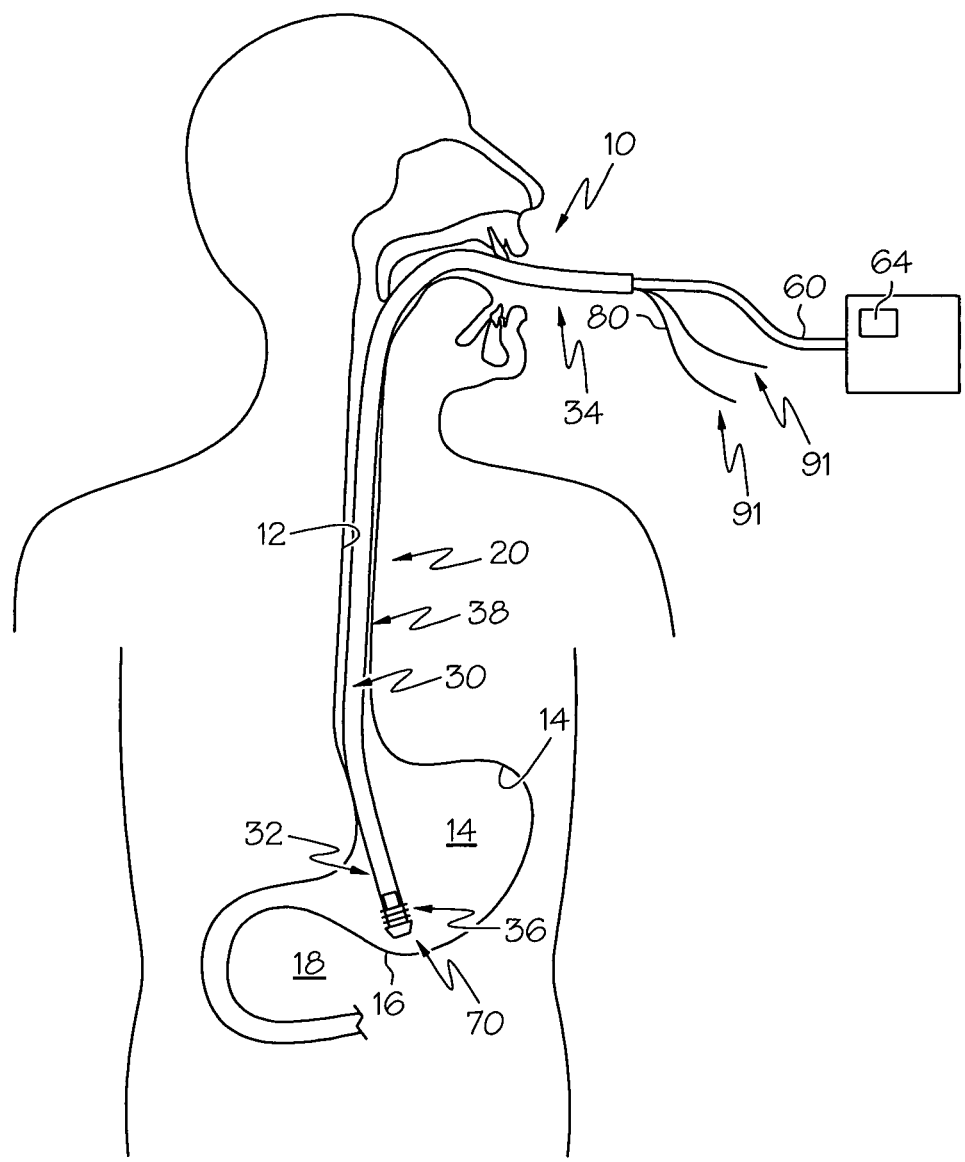
FIG. 1 is a diagrammatical view illustrating the use of one embodiment of a surgical instrument of the present invention inserted through a patient's mouth and esophagus to create a sealable opening through the stomach wall.

FIG. 1 illustrates, in general form, one exemplary surgical instrument 20 of the present invention that can be inserted through a natural orifice to form an opening through the wall of an organ. In the example depicted in FIG. 1, the instrument 20 is inserted through the mouth 10 and esophagus 12 into the stomach 14 to form an opening through the stomach wall 16. Those of ordinary skill in the art will again appreciate, however, that the various embodiments and methods of the present invention may be effectively employed to form openings through other types of organs without departing from the spirit and scope of the present invention.

In various embodiments, the instrument 20 may comprise an overtube 30 that consists of a substantially hollow tubular member 32 that has a proximal end 34 and a distal end 36. The hollow tubular member 32 may be fabricated from, for example, nylon or high density polyethylene plastic or similar materials. The hollow tubular member 32 has a hollow passage 38 therethrough for receiving and supporting surgical instruments such as, for example, a conventional endoscope 60. A variety of different types of endoscopes are known and, therefore, their specific construction and operation will not be discussed in great detail herein. In various embodiments, the endoscope 60 may operably support a video camera (not shown) that communicates with a video display unit 64 that can be viewed by the surgeon during the operation. The endoscope 60 may further have one or more working channels (not shown) extending therethrough for receiving various types of surgical instruments such as a hole-forming device 68, for example. See FIG. 8. The hole-forming device 68 may comprise, for example, a conventional Sphinctorotome, a needle knife or other incisor-type instrument that may be inserted through a working channel in the endoscope 60.

Figure 2:
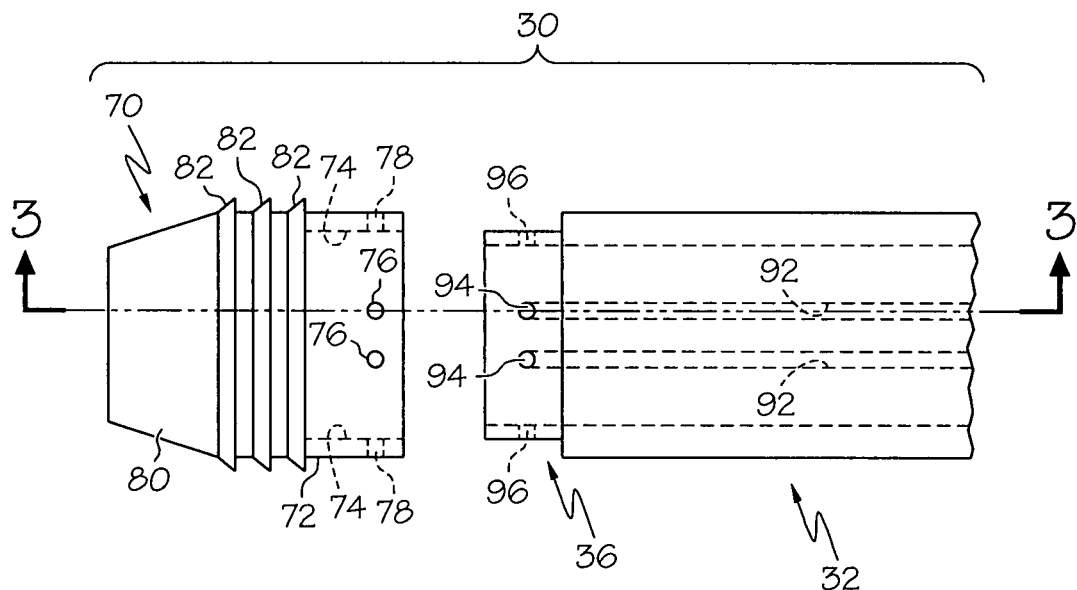
FIG. 2 is an exploded assembly view of the distal end of an overtube and an implantable tip of various embodiments of the present invention.
Figure 3:
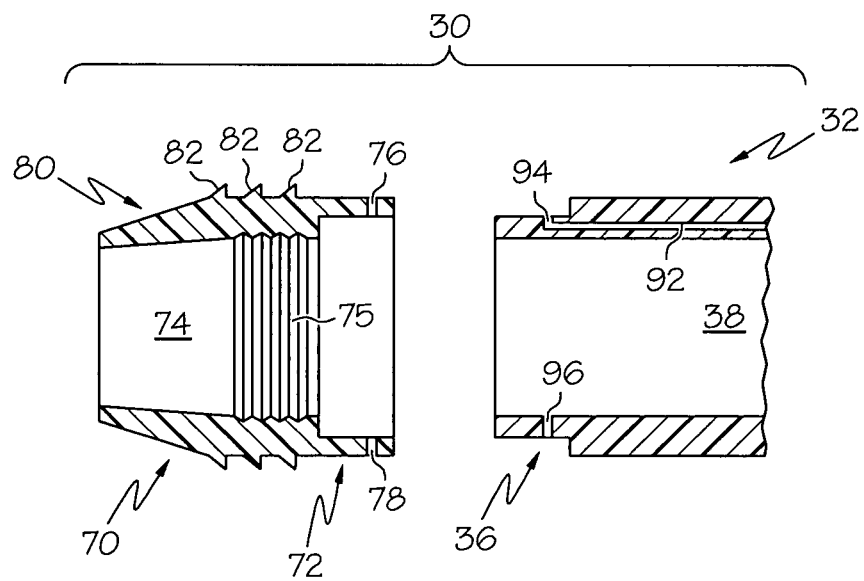
FIG. 3 is a cross-sectional view of the overtube and implantable tip of FIG. 2 taken along line 3-3 in FIG. 2.
Figure 4:
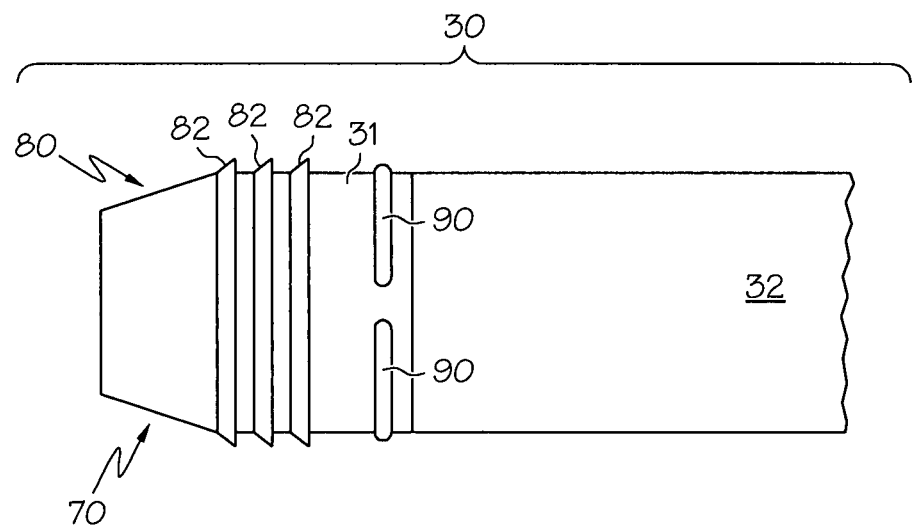
FIG. 4 is a partial assembled view of the overtube and implantable tip depicted in FIGS. 2 and 3.

Various embodiments of the surgical instrument 20 may further include an implantable tip 70 that is detachably affixed to the distal end 36 of the hollow tubular member 32. The implantable tip 70 may be fabricated from, for example, silicone, polycarbonate, urethane, stainless steel, etc. As can be seen in FIGS. 2 and 3, the implantable tip 70 may have a proximal end portion 72 sized to be received on the distal end 36 of the hollow tubular member 32. The implantable tip 70 has a lumen or passage 74 extending therethrough that may be substantially coaxially aligned with the hollow passage 38 in the hollow tubular member 32 when the implantable tip 70 is attached to the distal end 36 thereof. In the embodiments depicted in FIGS. 2-4 and 6-11, the implantable tip 70 is detachably retained on the distal end 36 of the hollow tubular member 32 by a string 90. The string 90 may comprise a string or cord manufactured from, for example, nitinol, prolene (suture), or braided stainless steel.

More specifically, in various embodiments the distal end 36 of the hollow tubular member 32 may have two passages 92 that extend therethrough and communicate with two radially extending holes 94 in the distal end 36 of the hollow tubular member 32. See FIG. 2. The radially extending holes 94 correspond to holes 76 in the proximal end 72 of the implantable tip 70. The distal end 36 of the hollow tubular member 36 may have additional radially extending holes 96 therethrough that correspond to holes 78 in the distal end 72 of the implantable tip 70. The implantable tip 70 may then be selectively retained on the distal end 36 of the hollow tubular member 32 by threading or sewing the string 90 through the aligned holes 94, 76 and aligned holes 96, 78 and passing the two ends 91 of the string 90 through the passages 92 so that they are accessible to the surgeon outside of the natural orifice 10. See FIG. 1. In alternative embodiments, the string 90 may pass through the hollow passage 38 in the hollow tubular member 32 instead of through passages 92 formed in the wall of the hollow tubular member 32. Thus, during the surgical procedure, the implantable tip 70 is retained on the distal end 36 of the hollow tubular member 32 by the string 90. When the surgeon desires to detach the implantable tip 70 from the hollow tubular member 32, the surgeon may simply pull one end 91 of the string 90 until it is unthreaded from the implantable tip 70.

Figure 5:
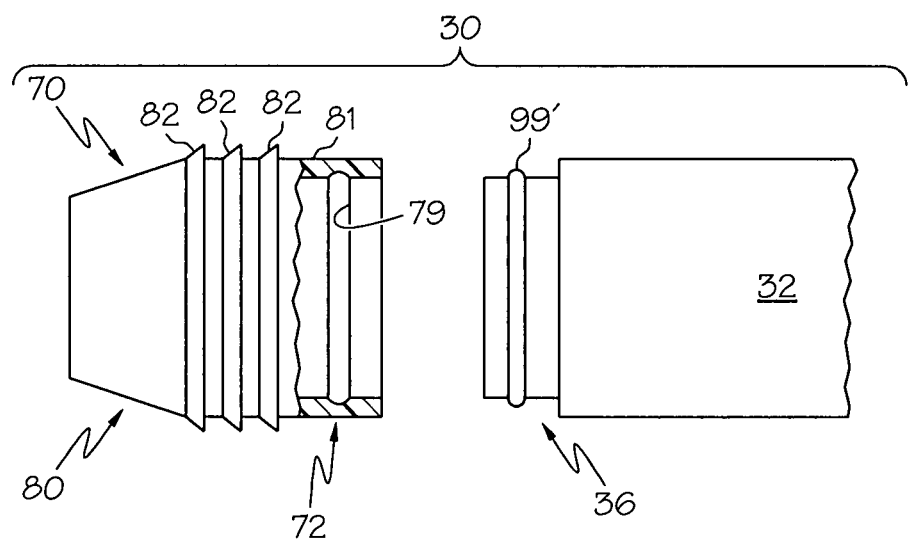
FIG. 5 is an exploded assembly view of a portion of another overtube and implantable tip embodiment of the present invention.

In alternative embodiments, the proximal end 72 of the implantable tip 70 may be detachably retained on the distal end 36 of the hollow tubular member 32 by a frictional fit created therebetween or, for example, by at least one detent in the form of a rib 99' formed on the distal end 36 of the hollow tubular member 32. The rib 99' is sized to be frictionally received in a circumferentially extending pocket 79' formed in the proximal end 72 of the implantable tip 70 as illustrated in FIG. 5. In other embodiments, the rib 99' may be formed on the implantable tip 70 and the pocket formed in the distal end 36 of the hollow tubular member 32. In yet other embodiments, one or more detents may be provided on one of the implantable tip 70 and the distal end 36 of the hollow tubular member 32 received in corresponding pockets in the other of the implantable tip 70 and the hollow tubular member 32. As used herein, the term "detent" is meant to encompass a continuous rib, a segmented rib, a single round or oval member or a series of such members. In other embodiments, the implantable tip 70 may be detachably supported on the distal end 36 of the hollow tubular member 32 by an appropriate adhesive material.

In various embodiments, for example, after the tip 70 has been implanted in the organ wall 16, the hollow tubular member 32 is detached from the tip 70 as will be discussed in further detail below. The hollow tubular member 32 may be detached from the implanted tip 70 by applying a retraction force in the proximal direction "PD" to the proximal end of the hollow tubular member 32. In some applications, for example, to prevent the tip 70 from being dislodged from the organ wall 16 when the hollow tubular member 32 is being detached therefrom, it may be desirable for the hollow tubular member 32 to be constructed to be released from the tip 70 upon application of retraction force to the tube 32 that does not exceed approximately two pounds.

As can also be seen in FIGS. 2-11, the implantable tip 70 may also have a distal end 80 that is substantially frusto-conically shaped. Also in various embodiments, at least one retention member, which may take the form of a barb 82 or other suitable formation, may be formed around the an outer surface 81 of the implantable tip 70 for retaining the implantable tip 70 within the organ wall 16 as will be discussed in further detail below.

Figure 6:
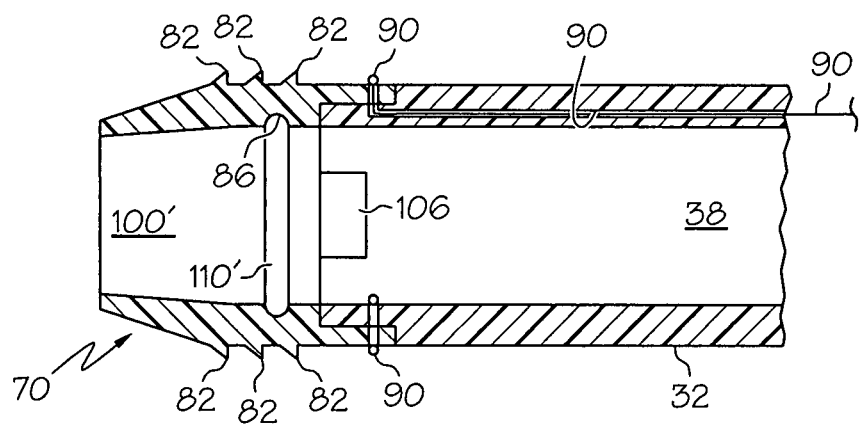
FIG. 6 is a cross-sectional view of another implantable tip and overtube embodiment of the present invention with a plug embodiment of the present invention installed within the implantable tip.
Figure 7:
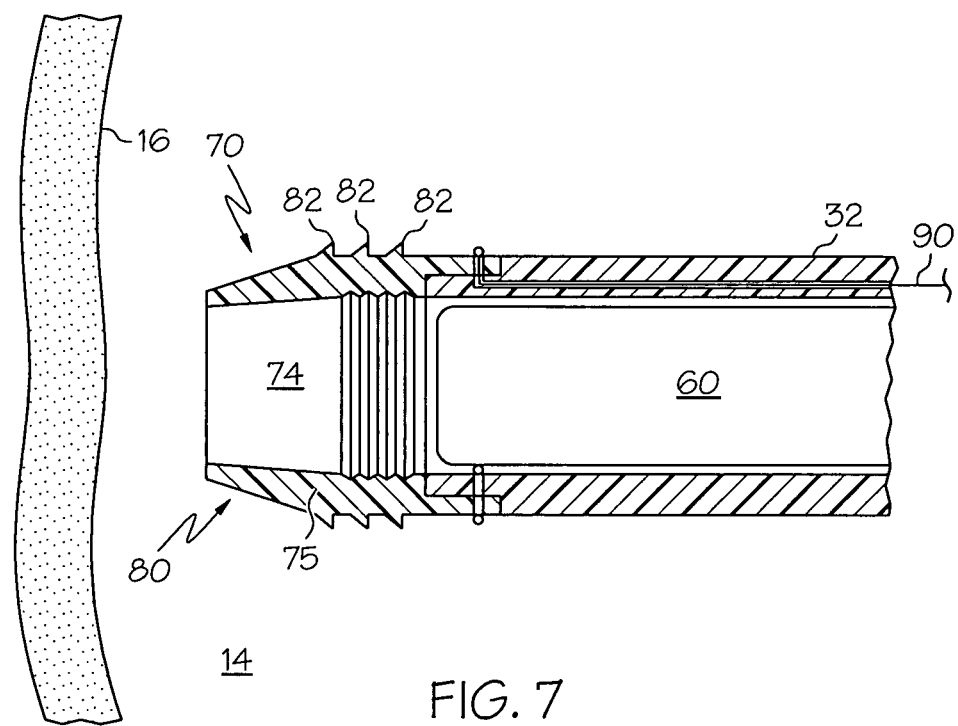
FIG. 7 is a cross-sectional view of the overtube and implantable tip of the embodiments depicted in FIGS. 2-4 with the distal end of the implantable tip positioned adjacent the wall of an organ.
Figure 10:
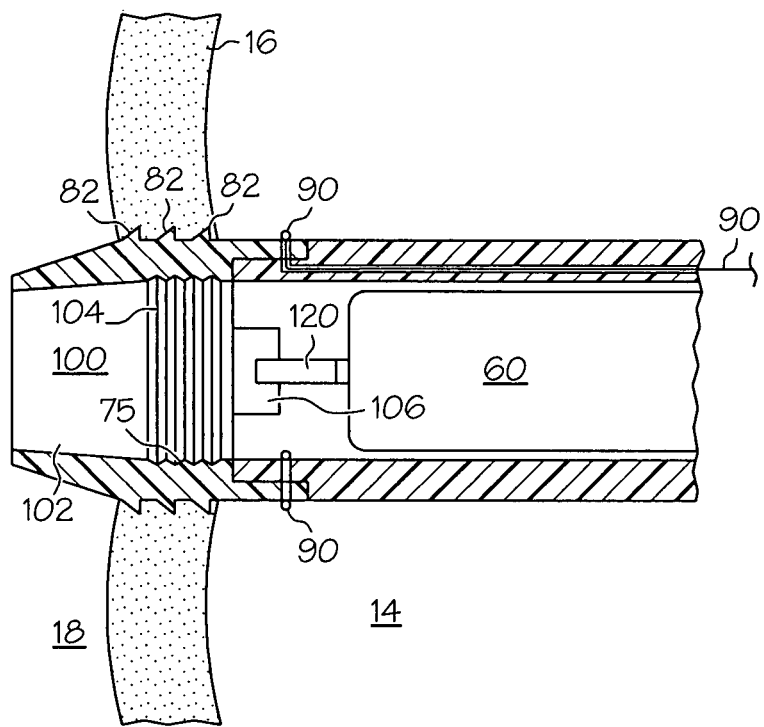
FIG. 10 is another cross-sectional view of the implantable tip and overtube of FIGS. 7-9 with a plug installed in the implantable tip.
Figure 11:
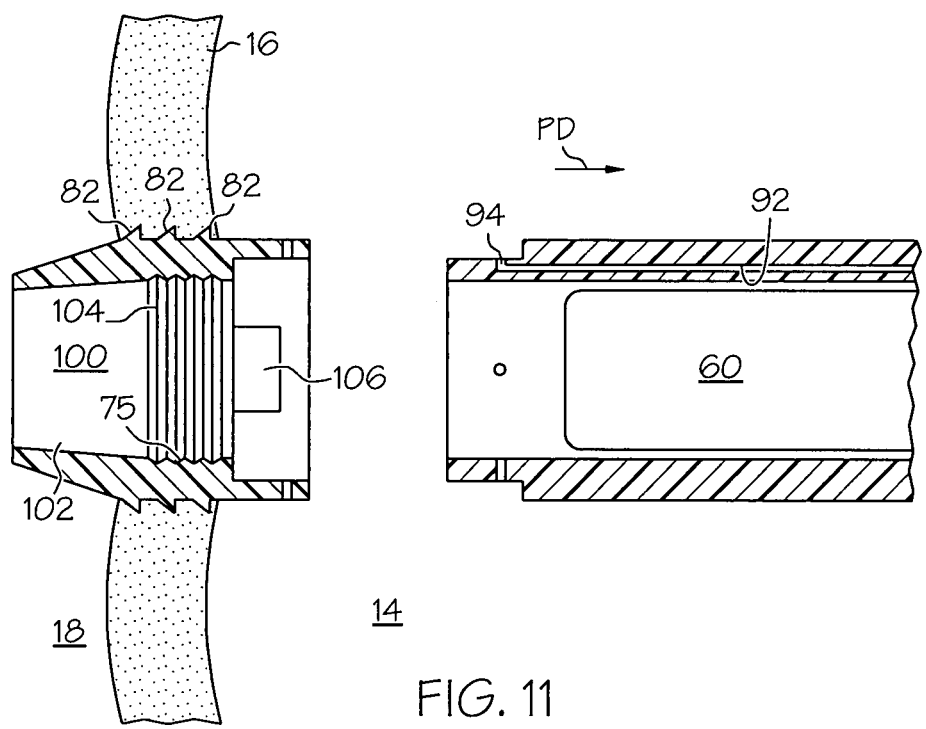
FIG. 11 is another cross-sectional view of the plugged implantable tip of FIG. 10 with the overtube detached from the implantable tip.

Also in various embodiments, a seal or plug member 100 may be provided to seal off or plug the lumen 74 in the implantable tip 70 after the surgical procedures have been completed within the body cavity 18, while, in some embodiments, affording the surgeon with the ability to remove the plug 100 to reopen the lumen 74 if necessary. As can be seen in FIGS. 10 and 11, in some embodiments, the plug 100 may have a body portion 102 that has a series of threads 104 formed thereon for threaded engagement with internal threads 75 formed in the implantable tip 70. The plug 100 may also have an installation tab 106 formed on a proximal end thereof to enable the plug to be gripped by an installation tool. In various embodiments, the plug 100 may be fabricated from, for example, silicone, polycarbonate, urethane, stainless steel, etc. FIG. 6 illustrates an alternative plug 100' that has a detent in the form of rib 110' thereon that is oriented to be frictionally received in a circumferentially extending groove 86' formed in the wall of the implantable tip 70. In still other embodiments, the plug 100 may be retained in position by a frictional fit or by an appropriate adhesive material.

Figure 8:
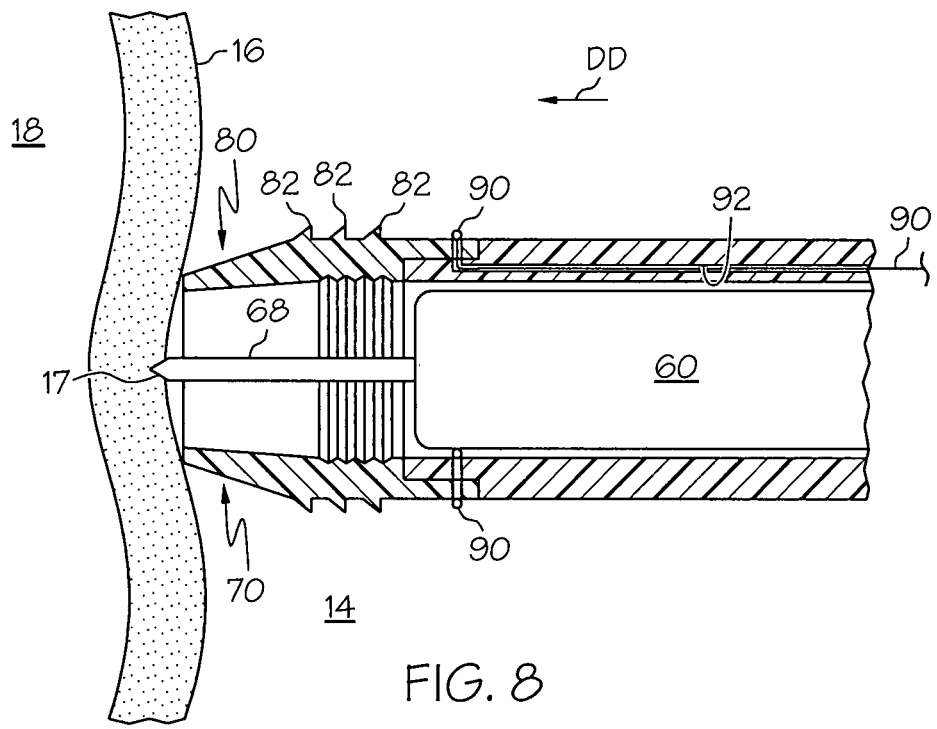
FIG. 8 is another cross-sectional view of the overtube and implantable tip of FIG. 7 with a hole-forming instrument extending through an endoscope positioned within the overtube to form an incision in the organ wall.
Figure 9:
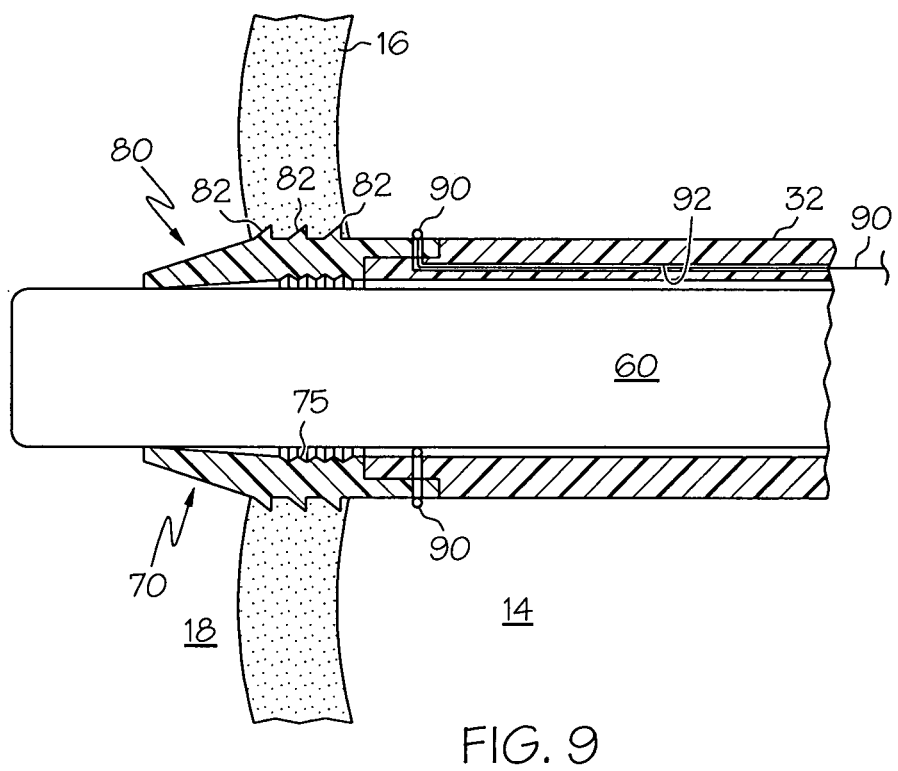
FIG. 9 is another cross-sectional view of the implantable tip and overtube of FIG. 7 with the tip implanted in the organ wall and the endoscope extending therethrough into a body cavity.

Use of the various surgical instrument embodiments of the present invention will now be described with reference to FIGS. 1 and 7-11. As can be seen in FIG. 1, the instrument 20 may be passed through the patient's mouth 10 into the stomach 14 such that the distal end 80 of the implantable tip 70 is adjacent the stomach (or organ) wall 16. See also FIG. 7. The surgeon may pass the endoscope 60 into the passage 38 in the hollow tubular member 32 to locate the specific surgical site on the stomach wall 16. Thereafter, the distal end 80 of the implantable tip 70 is pressed into the stomach wall 16 and the hole-forming instrument 68 may be passed through a working channel in the endoscope 60 to make an incision 17 in the stomach wall 16 as shown in FIG. 8. After an incision 17 has been made in the stomach wall 16, the surgeon forces the implantable tip 70 through the stomach wall 16 by applying a force to the hollow tubular member 32 in the distal direction "DD" until the barbs 82 of the implantable tip 70 are in retaining engagement with the stomach wall 16 as shown in FIG. 9. After the implantable tip 70 has been installed as shown in FIG. 9, the surgeon may then pass the distal end of the endoscope 60 through the lumen 74 in the implantable tip 70 into the body cavity 18 to perform other surgical procedures.

After the surgical procedure is completed within the body cavity 18, the surgeon may use surgical forceps 120 or other suitable surgical instruments that are passed through the working channel in the endoscope 60 to grip the installation tab 106 of a plug 100 and pass the plug 100 through the passage 38 in the hollow tubular member 32 to bring the plug 100 into sealing engagement with the implanted tip 70 as shown in FIG. 10. The forceps 120 may be used to screw the plug 100 into sealing engagement within the implantable tip 70 (for the embodiments depicted in FIGS. 3 and 7-11) or in alternative embodiments, the surgeon may use the forceps 120 to apply an installation force to the plug 100' to sealingly seat the plug 100' within the implantable tip 70. See FIG. 6.

Once the plug 100 or 100' has been installed within the implantable tip, the forceps 120 and endoscope 60 may be withdrawn form the hollow tubular member 32. The surgeon may then pull one end 91 of the string 90 to cause the string 90 to unthread from the holes in the tip 70 and the distal end 36 of the hollow tubular member 32. After the string 90 has been unthreaded from the tip 70 and the distal end 36 of the hollow tubular member, the surgeon may then withdraw the hollow tubular member 32, leaving the plugged tip 70 implanted in the organ wall 16 as shown in FIG. 11.

As can be appreciated from the foregoing discussion, the unique and novel features of various embodiments of the present invention afford the surgeon with the ability to form an opening through an organ wall by using an endoscope and other surgical instruments inserted through a patient's natural orifice. After completing the surgical procedures, the surgeon may seal off the opening by inserting a plug into the lumen of the implanted tip. In various embodiments, the plug may be selectively removed from the implanted tip to provide access therethrough if needed.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. Those of ordinary skill in the art will readily appreciate the different advantages provided by these various embodiments. For example, the use of the various embodiments of the present invention enables a surgeon to form a sealable passage through the wall of an organ by utilizing tools and instruments that may be passed into the body through a natural orifice.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. An overtube for use with an endoscope in a surgical procedure, said overtube comprising:
    a hollow tubular member having a proximal end and a distal end;
    an implantable tip detachably affixed to said distal end of said hollow tubular member, said implantable tip having an organ engagement portion for retaining said implantable tip within an organ wall, wherein said implantable tip comprises a lumen extending therethrough such that said lumen forms a passage through said organ wall; and
    sealing means for selectively unsealing said lumen of said implantable tip, wherein said sealing means is selectively and separably removable from said lumen of said implantable tip, and wherein said sealing means comprises a plug member, wherein said plug member comprises external mating threads, and wherein said lumen comprises internal mating threads for mating engagement with said external mating threads of said plug member.

2. The overtube of claim 1 wherein said implantable tip has a substantially frusto-conically shaped distal end.

3. The overtube of claim 1 further comprising at least one retention member on said organ engagement portion of said implantable tip for retaining said implantable tip in the organ wall.

4. The overtube of claim 1 wherein said implantable tip is attached to said distal end of said hollow tubular member by at least one detent member on at least one of said implantable tip and said distal end of said hollow tubular member.

5. An overtube for use with an endoscopic surgical instrument, said overtube comprising:
    a hollow tubular member having a distal portion;
    an implantable tip detachably affixed to said distal portion of said hollow tubular member, said implantable tip having an organ engagement portion for retaining said implantable tip within an organ wall, wherein said implantable tip comprises a lumen extending therethrough; and
    a plug member configured to selectively unseal said lumen of said implantable tip, wherein said plug member is selectively and separably removable from said lumen of said implantable tip, and wherein said plug member comprises external mating threads, and wherein said lumen comprises internal mating threads for mating engagement with said external mating threads of said plug member.

* * * * *

UNITED STATES PATENT AND TRADEMARK OFFICE
CERTIFICATE OF CORRECTION

| | | |
|---|---|---|
| PATENT NO. | : 8,480,657 B2 | Page 1 of 1 |
| APPLICATION NO. | : 11/981070 | |
| DATED | : July 9, 2013 | |
| INVENTOR(S) | : Gregory J. Bakos | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1462 days.

Signed and Sealed this
Twenty-seventh Day of January, 2015

Michelle K. Lee
*Deputy Director of the United States Patent and Trademark Office*